United States Patent
Cooley et al.

(10) Patent No.: US 10,590,712 B1
(45) Date of Patent: *Mar. 17, 2020

(54) SYSTEMS AND METHODS FOR MOUNTING A CUTTER IN A DRILL BIT

(71) Applicant: US Synthetic Corporation, Orem, UT (US)

(72) Inventors: Craig H. Cooley, Saratoga Springs, UT (US); Keith Baskett, Pleasant Grove, UT (US)

(73) Assignee: US SYNTHETIC CORPORATION, Orem, UT (US)

( * ) Notice: Subject to any disclaimer, the term of this patent is extended or adjusted under 35 U.S.C. 154(b) by 14 days.

This patent is subject to a terminal disclaimer.

(21) Appl. No.: 15/729,343

(22) Filed: Oct. 10, 2017

Related U.S. Application Data

(63) Continuation of application No. 14/669,793, filed on Mar. 26, 2015, now Pat. No. 9,803,427.

(60) Provisional application No. 61/971,392, filed on Mar. 27, 2014.

(51) Int. Cl.
| | | |
|---|---|---|
| *E21B 10/46* | (2006.01) |
| *E21B 10/52* | (2006.01) |
| *E21B 10/55* | (2006.01) |
| *E21B 10/56* | (2006.01) |
| *E21B 10/573* | (2006.01) |
| *E21B 10/62* | (2006.01) |
| *E21B 10/633* | (2006.01) |

(52) U.S. Cl.
CPC .............. *E21B 10/56* (2013.01); *E21B 10/46* (2013.01); *E21B 10/52* (2013.01); *E21B 10/55* (2013.01); *E21B 10/573* (2013.01); *E21B 10/62* (2013.01)

(58) Field of Classification Search
CPC .......... E21B 10/46; E21B 10/52; E21B 10/55; E21B 10/56; E21B 2010/561; E21B 2010/564; E21B 10/573; E21B 10/62; E21B 2010/624; E21B 10/633
See application file for complete search history.

(56) References Cited

U.S. PATENT DOCUMENTS

| | | | |
|---|---|---|---|
| 3,783,721 | A | 1/1974 | Miller |
| 4,014,595 | A | 3/1977 | Dolezal |
| 4,055,225 | A | 10/1977 | Milsapps |
| 4,211,292 | A | 7/1980 | Evans |
| 4,727,942 | A | 3/1988 | Galle et al. |
| 5,072,795 | A | 12/1991 | Delgado et al. |

(Continued)

*Primary Examiner* — Cathleen R Hutchins
(74) *Attorney, Agent, or Firm* — Dorsey & Whitney LLP

(57) ABSTRACT

Rotary drill bits may include on or more cutting element assemblies which include a cutter and a mounting system. In one embodiment, the mounting system includes a housing, a first bearing component disposed within the housing, and a second bearing component associated with the cutting element. In certain embodiments, the bearing components may comprise a table of superhard material bonded with a substrate. In one or more embodiments, the bearing components may include bearing surfaces that are arcuate. For example, the bearing surfaces may be substantially spherical (a portion of a sphere). The bearing components may be arranged to act as a radial bearing as well as a thrust bearing for the cutting element, enabling the cutting element to rotate about a longitudinal axis of the cutter, relative to the housing, while also enabling the longitudinal axis of the cutter to be displaced (change angles) relative to the housing.

18 Claims, 12 Drawing Sheets

(56) References Cited

U.S. PATENT DOCUMENTS

| | | | |
|---|---|---|---|
| 5,904,211 | A | 5/1999 | Friant et al. |
| 6,056,072 | A | 5/2000 | Koltermann et al. |
| 6,698,536 | B2 | 3/2004 | Moran et al. |
| 7,762,359 | B1 | 7/2010 | Miess |
| 7,866,418 | B2 | 1/2011 | Bertagnolli et al. |
| 8,061,458 | B1 | 11/2011 | Bertagnolli et al. |
| 8,079,431 | B1 | 12/2011 | Cooley et al. |
| 8,297,382 | B2 | 10/2012 | Bertagnolli et al. |
| 2005/0183892 | A1* | 8/2005 | Oldham .................. E21B 7/20 175/402 |
| 2007/0278017 | A1 | 12/2007 | Shen et al. |
| 2009/0236147 | A1 | 9/2009 | Koltermann et al. |
| 2011/0284293 | A1 | 11/2011 | Shen et al. |
| 2012/0273281 | A1 | 11/2012 | Burhan et al. |
| 2013/0140094 | A1 | 6/2013 | Burhan et al. |
| 2013/0146367 | A1 | 6/2013 | Zhang et al. |
| 2013/0292185 | A1 | 11/2013 | Knull et al. |

\* cited by examiner

SYSTEMS AND METHODS FOR MOUNTING A CUTTER IN A DRILL BIT

The present application is a continuation of U.S. patent application Ser. No. 14/669,793 entitled SYSTEMS AND METHODS FOR MOUNTING A CUTTER IN A DRILL BIT, filed on Mar. 26, 2015, which claims the priority of a provisional application Ser. No. 61/971,392, filed Mar. 27, 2014, the disclosures of each of which are hereby incorporated by reference in their entireties.

BACKGROUND

Rotary drill bits employing polycrystalline diamond compact ("PDC") cutters are often employed for drilling subterranean formations. Conventional PDC cutters may comprise a diamond table formed under ultra high temperature, ultra high pressure conditions onto a substrate, typically of cemented tungsten carbide. Conventional drill bit bodies may be formed of steel or may comprise a so-called tungsten carbide matrix including tungsten carbide particles distributed within a binder material.

Tungsten carbide matrix drill bit bodies may be fabricated by preparing a mold that embodies the inverse of the desired generally radially extending blades, cutting element sockets or pockets, junk slots, internal watercourses and passages for delivery of drilling fluid to the bit face, ridges, lands, and other external topographic features of the drill bit. Particulate tungsten carbide may then be placed into the mold and a binder material, such as a metal including copper and tin, may be melted into the tungsten carbide particulate and solidified to form the drill bit body. Steel drill bit bodies may be fabricated by machining a piece of steel to form generally radially extending blades, cutting element sockets or pockets, junk slots, internal watercourses and passages for delivery of drilling fluid to the bit face, ridges, lands, and other external topographic features of the drill bit.

In both matrix-type and steel bodied drill bits, a threaded pin connection may be formed for securing the drill bit body to the drive shaft of a downhole motor or directly to drill collars at the distal end of a drill string rotated at the surface by a rotary table, top drive, drilling motor or turbine.

Conventional cutting element retention systems or structures that have been employed generally comprise two different styles. One style includes tungsten carbide studs comprising a cylindrical tungsten carbide cylinder having a face oriented at an angle (back rake angle) with respect to the longitudinal axis of the cylinder, the face carrying a superabrasive cutting structure thereon. The cylinder may be press-fit or brazed into a recess formed in the bit that is generally oriented perpendicularly to the blades extending from the bit body on the bit face. A second type of retention system includes the brazed attachment of a generally cylindrical cutting element into a recess (e.g., a cutter pocket) formed on the bit face, typically on a blade extending from the bit face.

Generally speaking, the first cutting element retention style described above is designed for a stud type cutting element, while the second cutting element retention style described above is designed for generally cylindrical cutting elements, such as PDC cutters. In either system, the orientation of the cutting elements is conventionally held stationary relative to the bit body as the drill bit is used. Of the two different types of cutting element retention configurations utilized in the manufacture of rotary drill bits, cylindrical cutting elements are generally more common. Stud-type cutting elements, on the other hand, are relatively uncommon and may require a brazing or infiltration cycle to affix the PDC or TSPs to the stud.

SUMMARY

The present invention relates generally to cutting element assemblies used, for example, in subterranean drill bits. In one example embodiment, a cutting element assembly is provided that comprises a cutting element and a mounting system. The mounting system includes a housing having a pocket formed therein, the pocket being sized and configured to receive a portion of the cutting element. The mounting system further includes at least one radial bearing component between the cutting element and the housing and at least one thrust bearing component between the cutting element and the housing.

In one embodiment, the cutting element assembly may include a retaining member configured to retain the cutting element within the cavity.

In one embodiment, the cutting element and the housing are arranged such that a clearance gap is maintained between the cutting element and the housing. In certain embodiments, at least one seal is disposed between the housing and the cutting element. The cutting element and the at least one seal may be arranged to maintain a pressure within the cavity within a defined range.

In one embodiment, the cutting element is substantially cylindrical and includes a plurality of grooves formed in a peripheral region of the cutting element. In one embodiment the plurality of grooves are each at least partially formed in a side surface of the cutting element. In another embodiment, the plurality of grooves are each at least partially formed in a face surface of the cutting element.

In another embodiment, the cutting element assembly may include a vibrational member coupled with the cutting element, the vibrational member being configured to induce vibration between the cutting element and the housing when external cutting forces are applied to the cutting element.

In one embodiment, the housing includes at least one passage for communication with a pressure compensating system.

In one embodiment, the assembly further includes at least one lip seal between the housing and the cutting element.

In one embodiment, the first bearing component includes a substantially spherical bearing surface. In another embodiment, the second bearing component may include a substantially spherical bearing surface.

In one embodiment, at least one of the first bearing component and the second component comprises a table of superhard material bonded to a substrate, wherein a bearing surface is formed in the table of superhard material.

In one embodiment a plurality of bearing elements are disposed between the first bearing component and the second bearing component. The plurality of bearing elements may be configured, for example, as rolling elements such as ball bearings or as needle bearings.

In one embodiment, the housing includes a first housing component and a second housing component, and wherein the first housing component and the second housing component are removably coupled with one another.

In accordance with another aspect of the invention, a rotary drill bit for drilling a subterranean formation is provided. The drill bit includes a bit body and at least one cutting element assembly coupled with the bit body. The cutting element assembly comprises a cutting element; a housing having a pocket formed therein, the pocket being sized and configured to receive a portion of the cutting element; a first bearing component; and at least a second bearing component, wherein the first bearing component and the at least second bearing component are configured to act, independently or collectively, as a radial bearing and a thrust bearing between the cutting element and the housing.

In one embodiment, the housing is brazed to the bit body. In one embodiment, the housing may be formed of two or more components, with a first component being brazed to the bit body and at least one other component being removably coupled with the first component.

The cutting element assembly may further include additional features such as set forth above, or as described in the detailed description and associated drawings.

In accordance with another aspect of the present invention, a cutting element assembly is provided. The cutting element assembly includes a cutting element and a mounting system. The mounting system includes a housing having a pocket formed therein, the pocket being sized and configured to receive a portion of the cutting element. The mounting assembly further includes at least one bearing component, wherein the at least one bearing component is configured to act as a radial bearing and a thrust bearing between the cutting element and the housing.

In accordance with one embodiment, the at least one bearing component includes a tapered bearing surface.

In accordance with one embodiment, the at least one bearing component includes a bearing surface that includes a portion of a substantially conical surface.

Features from any of the various embodiments described herein may be used in combination with one another, without limitation. In addition, other features and advantages of the instant disclosure will become apparent to those of ordinary skill in the art through consideration of the ensuing description, the accompanying drawings, and the appended claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

Figure 1:
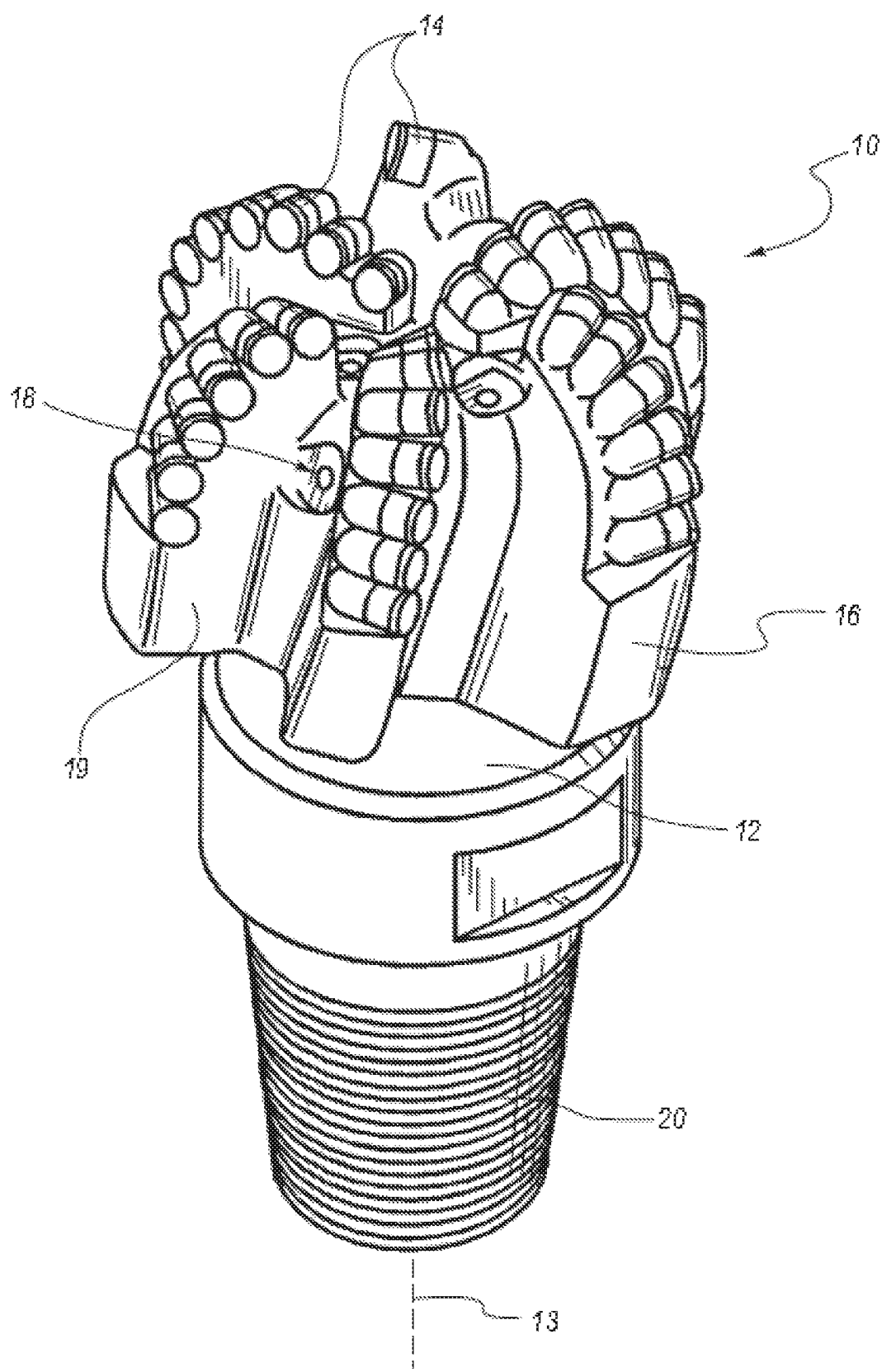
FIG. 1 is a perspective view of a rotary drill bit according to an embodiment of the present invention.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

The present invention relates generally to drill bits, such as rotary drill bits used for drilling subterranean formations. "Superhard," as used herein, refers to any material having a hardness that is at least equal to a hardness of tungsten carbide. Additionally, a "superabrasive material," as used herein, may refer to a material exhibiting a hardness exceeding a hardness of tungsten carbide, such as, for example, polycrystalline diamond. In addition, as used throughout the specification and claims, the word "cutting" generally refers to any drilling, boring, or the like. The word "cutting," as used herein, refers broadly to machining processes, drilling processes, or any other material removal process utilizing a cutting element.

Figure 2:
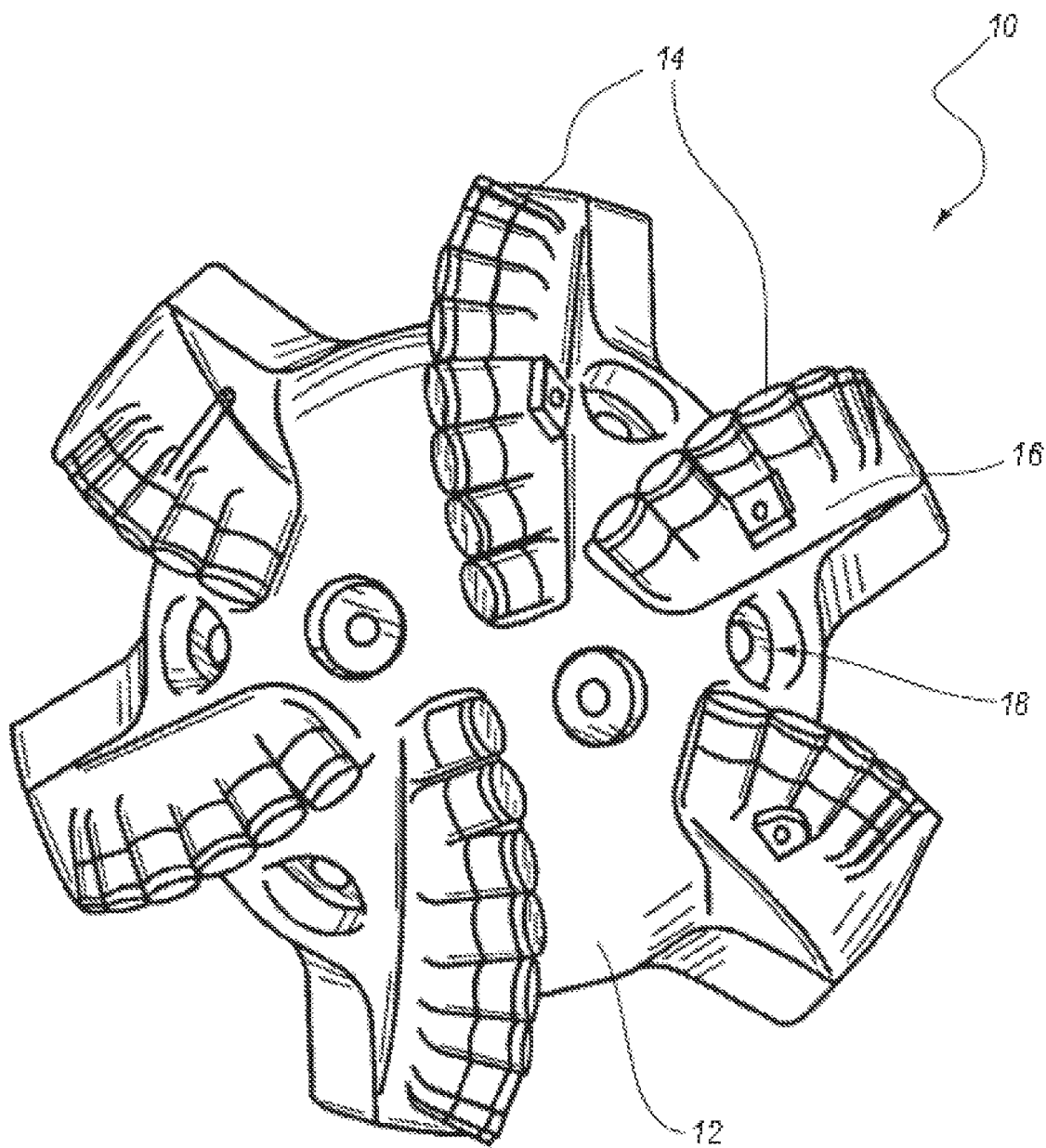
FIG. 2 is an end view of the rotary drill bit shown in FIG. 1.

Referring to FIGS. 1 and 2, a rotary drill bit 10 is shown according to an embodiment of the invention. FIG. 1 is a perspective view of the rotary drill bit 10 and FIG. 2 is a top or end view of the rotary drill bit 10. The rotary drill bit 10 is configured for drilling into a formation, such as a subterranean formation, or any other material to be drilled. As illustrated in FIGS. 1 and 2, the rotary drill bit 10 may comprise a bit body 12 having a rotational axis 13, one or more bit blades 16 having rotational leading faces 19 (i.e., the face of the blade that "leads" the blade when the blade is rotated about the axis in an intended rotational direction), and a threaded pin connection 20. A plurality of cutting elements 14 may be secured to bit body 12 of rotary drill bit 10 in a manner described in further detail below. Slots, sometimes referred to as junk slots, may be defined between circumferentially adjacent blades 16 and be configured to enable material, such as rock debris and drilling fluid, to be conveyed away from the drill bit during a drilling operation. One or more nozzle cavities 18 may be defined in rotary drill bit 10 and configured to convey drilling fluid that is passed through a drill string and through the drill bit body 12. The rotary drill bit 10 may rotate about rotational axis 13 during operation of the drill bit, such as when engaged with a subterranean formation.

As noted above, the cutting elements 14 may be mounted to various suitable portions of the drill bit body 12. For example, the cutting elements 14 may be mounted to portions of bit blades 16 and configured to contact a formation during a drilling operation. The cutting elements 14 may have cutting surfaces and cutting edges adjacent to and/or extending from the leading faces 19 of the blades 16 such that the cutting surfaces and cutting edges contact a formation while the rotary drill bit 10 is rotated about its rotational axis 13 during a drilling operation. The nozzle cavities 18 defined in the drill bit 10 may communicate with an interior portion of the drill bit 10 (e.g., a plenum or other fluid flow path) such that drilling fluid may be conveyed from within the drill bit body, through the nozzle cavities 18, past the cutting elements 14 and various exterior portions of bit body 12. It should be understood that FIGS. 1 and 2 merely depict one example of a rotary drill bit employing cutting element assemblies of the present invention (e.g., a cutting element 14 combined with a mounting assembly, including any of the example embodiments below), without limitation.

Figure 3:
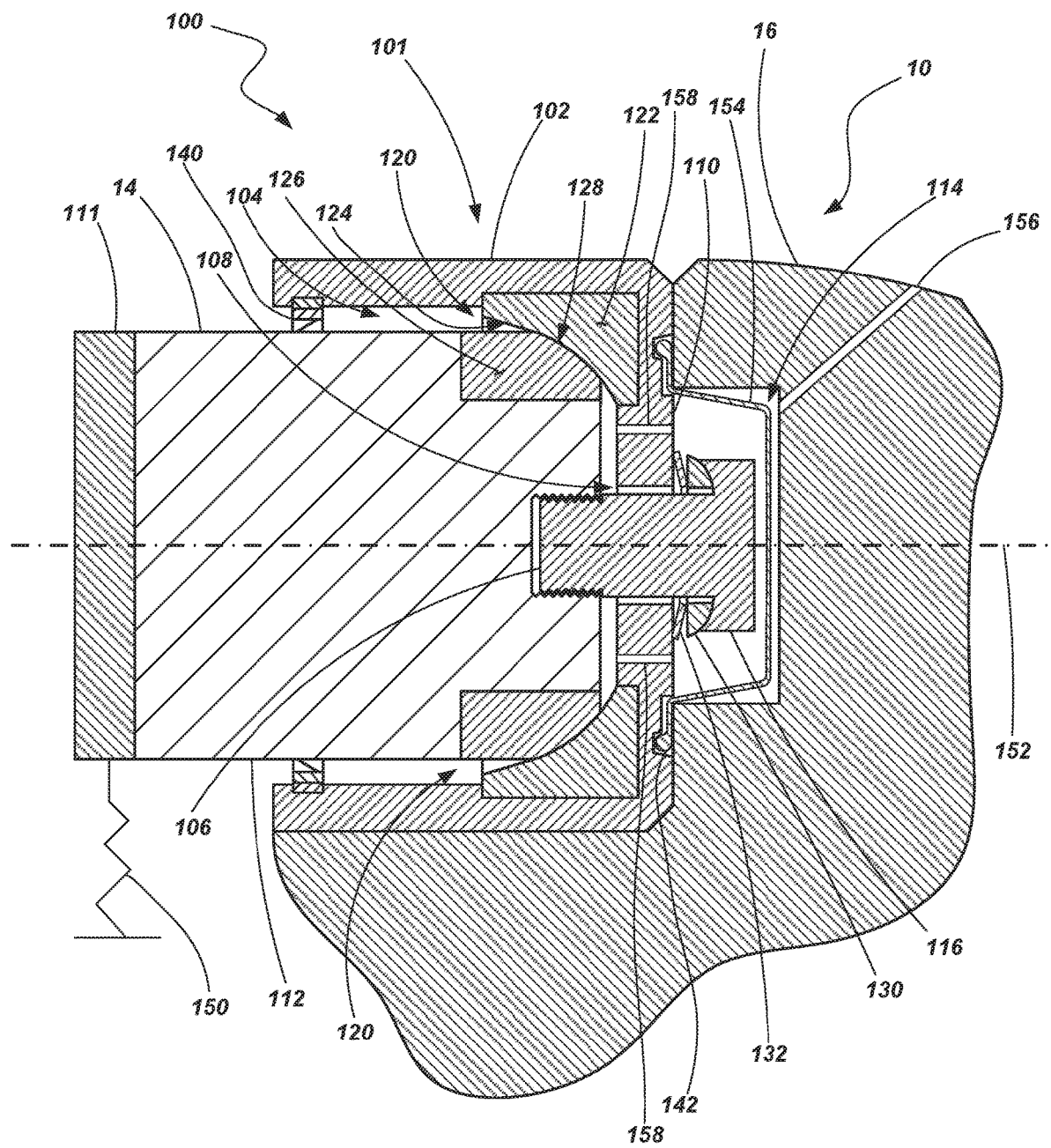
FIG. 3 is a cross-sectional view of a bearing assembly including a mounting system for mounting a cutting element to a drill bit in accordance with an embodiment of the present invention.

Referring now to FIG. 3, a cutting element assembly 100 is shown having a cutting element 14 and a mounting system 101 for mounting the cutting element 14 to a drill bit body 10. The mounting system 101 includes a housing 102 having a cavity 104 formed therein for receipt of a cutting element 14. In one embodiment, the cutting element 14 may be configured as a polycrystalline diamond compact (PDC) having a superabrasive table 111 of polycrystalline diamond bonded with a substrate 112 of a material such as cobalt-cemented tungsten carbide. Some non-limiting examples of cutting elements are described in U.S. Pat. No. 8,297,382 to Bertagnolli et al., issued Oct. 30, 2012, U.S. Pat. No. 8,079,431 to Cooley et al., issued Dec. 20, 2011, and U.S. Pat. No. 7,866,418 to Bertagnolli et al., issued Jan. 11, 2011, the disclosures of which are incorporated by reference herein in their entireties. It is noted, however, that the present invention is not limited to use with PDC type cutting elements and that a variety of other cutting elements may be utilized in the present invention.

In one embodiment, when formed as a PDC, a cutting element 14 may be formed by subjecting diamond particles in the presence of a catalyst to HPHT sintering conditions. The catalyst may be, for example, in the form of a powder, a disc, a foil, or in a cemented carbide substrate. The PDC may be formed independently from or integrally with a substrate, both under HPHT conditions.

For example, a PCD body or table 111 may be fabricated by subjecting a plurality of diamond particles 104 (e.g., diamond particles having an average particle size between 0.5 μm to about 150 μm) and the substrate 112 to a HPHT sintering process in the presence of a catalyst, such as a metal-solvent catalyst, cobalt, nickel, iron, a carbonate catalyst, an alloy of any of the preceding metals, or combinations of the preceding catalysts to facilitate intergrowth between the diamond particles and form the PCD table 111 comprising directly bonded-together diamond grains (e.g., exhibiting $sp^3$ bonding) defining interstitial regions with the catalyst disposed within at least a portion of the interstitial regions. In order to effectively HPHT sinter the plurality of diamond particles, the particles and substrate may be placed in a pressure transmitting medium, such as a refractory metal can, graphite structure, pyrophyllite or other pressure transmitting structure, or another suitable container or supporting element. The pressure transmitting medium, including the particles and substrate, may be subjected to an HPHT process using an HPHT press at a temperature of at least about 1000° C. (e.g., about 1300° C. to about 1600° C.) and a cell pressure of at least 4 GPa (e.g., about 5 GPa to about 10 GPa, or about 7 GPa to about 9 GPa) for a time sufficient to sinter the diamond particles and form a PCD table 111 that bonds to the substrate 112. In one embodiment, a PCD body or table 111 may be formed by sintering diamond particles in an HPHT process without a substrate present. A PCD body may be formed by sintering diamond particles in the presence of a catalyst not supplied from a substrate, by way of non-limiting example, a powder, a wafer, or a foil.

In one embodiment, when the table 111 is formed by sintering the diamond particles in the presence of the substrate 112 in a first HPHT process, the substrate 112 may include cobalt-cemented tungsten carbide from which cobalt or a cobalt alloy infiltrates into the diamond particles and catalyzes formation of PCD. For example, the substrate 112 may comprise a cemented carbide material, such as a cobalt-cemented tungsten carbide material or another suitable material. Nickel, iron, and alloys thereof are other catalysts that may form part of the substrate 112. The substrate 112 may include, without limitation, cemented carbides including titanium carbide, niobium carbide, tantalum carbide, vanadium carbide, and combinations of any of the preceding carbides cemented with iron, nickel, cobalt, or alloys thereof. However, as previously noted, in other embodiments, the substrate 112 may be replaced with a catalyst material disc and/or catalyst particles may be mixed with the diamond particles. In other embodiments, the catalyst may be a carbonate catalyst selected from one or more alkali metal carbonates (e.g., one or more carbonates of Li, Na, and K), one or more alkaline earth metal carbonates (e.g., one or more carbonates of Be, Mg, Ca, Sr, and Ba), or combinations of the foregoing. The carbonate catalyst may be partially or substantially completely converted to a corresponding oxide of Li, Na, K, Be, Mg, Ca, Sr, Ba, or combinations after HPHT sintering of the plurality of diamond particles. The diamond particle size distribution of the plurality of diamond particles may exhibit a single mode, or may be a bimodal or greater distribution of grain size. In one embodiment, the diamond particles may comprise a relatively larger size and at least one relatively smaller size. As used herein, the phrases "relatively larger" and "relatively smaller" refer to particle sizes (by any suitable method) that differ by at least a factor of two (e.g., 30 μm and 15 μm). According to various embodiments, the diamond particles may include a portion exhibiting a relatively larger average particle size (e.g., 50 μm, 40 μm, 30 μm, 20 μm, 15 μm, 12 μm, 10 μm, 8 μm) and another portion exhibiting at least one relatively smaller average particle size (e.g., 6 μm, 5 μm, 4 μm, 3 μm, 2 μm, 1 μm, 0.5 μm, less than 0.5 μm, 0.1 μm, less than 0.1 μm). In one embodiment, the diamond particles may include a portion exhibiting a relatively larger average particle size between about 10 μm and about 40 μm and another portion exhibiting a relatively smaller average particle size between about 1 μm and 4 μm. In some embodiments, the diamond particles may comprise three or more different average particle sizes (e.g., one relatively larger average particle size and two or more relatively smaller average particle sizes), without limitation.

When sintered using a catalyst material, the catalyst material may remain in interstitial spaces between the bonded diamond grains. In various embodiments, at least some of the catalyst material may be removed from the interstitial spaces of the superabrasive table 111. For example, catalyst material may be removed (such as by acid-leaching) to a desired depth from a working surface of the table 111. In one embodiment, catalyst material may be substantially removed from the table 111 from a working surface (e.g., a top surface, a side surface, or any surface expected to engage with a subterranean material during cutting/drilling activities) to a depth between approximately 50 μm to approximately 100 μm. In other embodiments, catalyst materials may be removed to a lesser depth or to a greater depth. Removal of the catalyst material to provide a substantially catalyst free region (or at least a catalyst-lean region) provides a table that is thermally stable by removing the catalyst material, which exhibits a substantially different coefficient of thermal expansion than the diamond material, in a region or the table expected to see substantial temperature increases during use. In one embodiment, the substantially interstitial areas of the catalyst-free region may The interstitial spaces of the catalyst-free region may remain substantially material free. In some embodiments, a second material (i.e., a material that is different from the catalyst material) may be introduced into the interstitial spaces from which catalyst material has been removed. Some examples of materials that may subsequently introduced into such interstitial spaces, and methods of introducing such materials into the interstitial spaces, are set forth in U.S. Pat. No. 8,061,485 to Bertagnolli et al., issued Nov. 22, 2011, the disclosure of which is incorporated by reference herein in its entirety.

Still referring to FIG. 3, in one embodiment, the housing 102 may be formed of a metal or a metal alloy material (e.g., steel or tungsten carbide). The housing 102 of the system may be positioned in pocket or recess formed within the bit body 12 and brazed or otherwise fixed or adhered to the bit body 12. The cavity 104 and cutter 14 may be configured such that a clearance gap (e.g., a substantially annular gap) remains between the inner sidewall surface of the housing and the outer side surface of the cutting element as seen in FIG. 3.

A mechanical fastener 106 may be used to retain the cutting element 14 within the cavity 104 of the housing 102. For example, a fastener 106 may extend through an opening 108 formed within a rear wall 110 of the housing 102 and threadably engage a substrate 112 (or other component such as a base member coupled with the substrate) of the cutting element 14. A cavity or pocket 114 may be formed in the bit body 12 (e.g., within a blade 16) to accommodate the head 116 of the fastener 106.

A bearing apparatus 120 enables the cutting element 14 to be rotationally mounted within the housing 102. The bearing apparatus 120 shown in FIG. 3 includes a first bearing component 122 that may be formed directly in the housing 102 or may be a separate component that is mounted within the housing 102. The first bearing component 122 includes an arcuate bearing surface 124 which, in one embodiment, may be configured as a substantially spherical surface (i.e., a portion of a surface of a sphere). The bearing surface 124 may be formed from a variety of different materials to provide a low friction and/or highly wear resistant bearing surface (e.g., chrome steel, stainless steel, silicon nitride, polycrystalline diamond or other metals or ceramics). It is noted that the bearing component 122 may comprise a single component (e.g., configured as an annulus) that, for example, substantially encircles a portion of the cutting element 14, or it may include a plurality of discrete components that are cooperatively positioned within the cavity of the housing 102 so as to effectively surround or encircle a portion of the cutting element 14.

The bearing apparatus 120 further includes a second bearing component 126 which may be formed directly in, or as a separate component that is coupled with, the back end of cutting element 14 (e.g., in the substrate 112). As with the first bearing component 122, the second bearing component 126 may be formed as a single component, or as a plurality of discrete components cooperatively arranged about the cutting element 14. The second bearing component 126 includes an arcuate bearing surface 128. In one embodiment, the arcuate bearing surface 128 may be configured to substantially conform with the shape of the bearing surface 124 of the first bearing component 122 (as seen in the cross-sectional view of FIG. 3). In another embodiment, the arcuate bearing surface 128 of the second bearing component 126 may exhibit a substantially smaller radius than the arcuate bearing surface 124 of the first bearing component 122 such that a limited point or line of contact exists between the two components 122 and 126. As with the bearing surface 124 of the first component 122, the bearing surface 128 of the second component may be formed of, or otherwise comprise, any of a variety of known low friction, high wear resistant or high strength bearing materials.

In one embodiment, the fastener 106 may be configured with a head 116 having a lower arcuate surface that engages with a mating seat. For example, the lower (engaging) surface of the head 116 may be shaped and configured to engage with a substantially spherical seat 130. Additionally, a spring retainer 132 may be associated with the spherical seat (either as a separate or integrated component). The spherical seat 130, along with the spring retainer 132, provides another bearing surface to allow for slight movement and/or reduce friction between the cutting element 14 (including the fastener 106) and the housing 102.

The mounting system 101 further includes a first seal 140 which may be coupled with the housing and configured to engage a surface of the cutting element 14. In one embodiment, the seal 140 may be constructed as a radial shaft seal (also referred to as a lip seal) and may be formed of a variety of materials. For example, the seal may include a lip (i.e., the portion that contacts the cutting element 14) that comprises a diamond material. Of course other materials are also contemplated. For example, the seal 140 may comprise metal elements, thermoplastic elements (e.g., polytetrafluoroethylene (PTFE)), or elastomeric elements. The seal 140 is configured to keep debris and contaminants (e.g., dirt and mud from the drilling environment) from entering into the cavity 104 and between the bearing surfaces 124 and 128. Additionally, the seal 140 may be configured to maintain the pressure within the cavity 102 at a desired level as it is anticipated that the environmental pressure external to the cavity will change while the drill bit 10 is operated at various depths or elevations within a well bore and is subjected to various fluid pressures during operation.

A second seal 142 may be positioned between the housing 102 and the bit body 102. In one embodiment, the seal 142 may be configured as an o-ring type seal. Since the pocket 114 in the bit body 102 and the cavity 104 within the housing are in communication with one another, the seal 142 may also serve to maintain a desired pressure within the pocket 114 and cavity 104.

A vibrational member 150 may be coupled between the bit body 12 and the cutting element 14 to facilitate rotation of the cutting element 14 within the housing 102 when cutting forces are applied to the cutting element 14 during operation of the drill bit 10. FIG. 3 shows the vibrational member 150 schematically as a simple spring. However, the vibrational member 150 may take a variety of forms. Some examples of vibrational members or assemblies are described in the previously incorporated U.S. Pat. No. 8,079,431 to Cooley et al. In some embodiments, the vibrational member 150 may be associated with other components or structural features to encourage rotation of the cutting element 14 in a first direction about an axis 152 relative to the housing 102 while inhibiting rotation of the cutting element 14 in a second, substantially opposite direction about the axis.

The mounting system 101 provides a cutting element 14 with a spherical radial and thrust bearing combination between it and the housing with the housing being mounted to the drill bit 10 rather than directly mounting the cutting element to the drill bit body. The support structure that is provided to the cutting element 14 relative to the housing enables the movement necessary, including the ability of the axis of rotation 152 to change angles relative to the housing 102, for the cutting element 14 to vibrate during drilling operations without impeding rotation of the cutting element 14 within the housing and, thus, relative to the bit body 12. The sealed environment enables the cutting element and bearings to be lubricated and, optionally, pressure compensated.

For example, a pressure compensation system may include a flexible membrane element 154 integrated with the seal 142. The membrane 154 may be positioned within the cavity 114 formed in the drill bit body 12 and enable any lubricant disposed within the cavity 104 of the housing 102 (and on the fastener 116 side of the membrane 154) to be pressure compensated during operation of the drill bit 10. A channel or passageway 156 may be in communication with the cavity 114 and extend through the bit body 12 to an external pressure. When pressures change (e.g., external pressure rises), the pressure change will be transmitted through the passageway 156 causing the membrane 154 to collapse toward the rear wall 110 of the housing, equalizing the pressure within the cavity 104 by way of communicating passageways 158 formed in the housing 102 (and/or by way of the opening 108 acting as a passageway between the two cavities 104 and 114) thereby preventing or inhibiting drilling mud or other debris from entering into the cavity past the seal 140. Similarly, if external pressure were to drop, such a pressure change would manifest itself by the membrane 154 expanding outwardly from the rear wall 110 of the housing 102 to equalize pressure within the cavity 114, preventing or limiting lubricant from escaping out of the cavity 104 past the seal 140. In other embodiments, other lubricant and pressure passageways may be formed in the housing 102, or in both the housing 102 and the drill bit body 12. For example, a membrane or other pressure-compensation mechanism may be in fluid of hydraulic communication with the cavity 104 of the housing 102 (e.g., via one or more through holes in housing 102 and/or passageways in drill bit body 12). Accordingly, such a pressure compensating mechanism may be positioned anywhere within a drill bit body as would be suitable.

Examples of various methods and systems for pressure compensation, as well as lubrication, are described by U.S. Patent Application No. 2009/0236147 to Kolterman et al., filed on Mar. 20, 2008, U.S. Pat. No. 6,698,536 to Moran et al., filed Feb. 20, 2002, U.S. Pat. No. 6,056,072 to Kolterman et al., filed on Nov. 2, 1998, U.S. Pat. No. 5,072,795 to Delgado et al., filed Jan. 22, 1991, U.S. Pat. No. 4,727,942 to Galle et al., filed Nov. 5, 1986, U.S. Pat. No. 4,014,595 to Dolezal, filed May 30, 1975, and U.S. Pat. No. 4,055,225 to Milsapps, filed May 17, 1976, the disclosures of each of which are incorporated by reference herein in its entireties.

Figure 4:
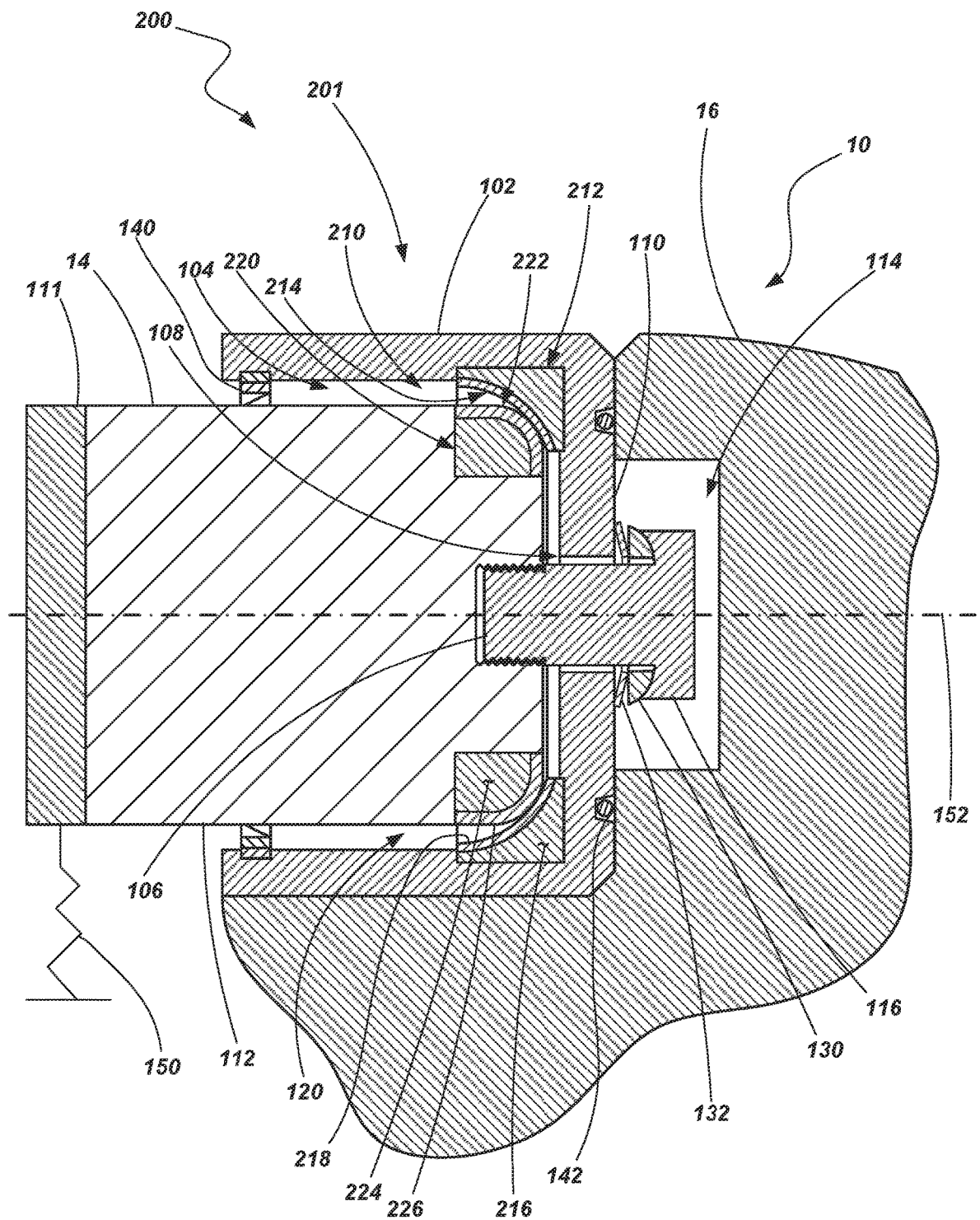
FIG. 4 is a cross-sectional view of a bearing assembly including a mounting system for mounting a cutting element to a drill bit in accordance with another embodiment of the present invention.

Referring to FIG. 4, a cutting element assembly 200, including a mounting system 201, is shown in accordance with another embodiment. The mounting system 201 includes a housing 102 having a cavity 104 formed therein for receipt of a cutting element 14. The housing 102 of the system may be positioned in pocket or recess formed within the bit body 12 and brazed or otherwise fixed to the bit body 12. The cavity 104 and cutter 14 may be configured such that a clearance gap (e.g., a substantially annular gap) remains between the inner sidewall surface of the housing and the outer side surface of the cutting element as seen in FIG. 4. A mechanical fastener 106 may be used to retain the cutting element 14 within the cavity 104 of the housing 102. For example, a fastener 106 may extend through an opening 108 formed within a rear wall 110 of the housing and threadably engage a substrate 112 (or other component, such as a base member coupled with the substrate) of the cutting element 14. A cavity or pocket 114 may be formed in the bit body 12 (e.g., within a blade 16) to accommodate the head 116 of the fastener 106. The mounting system 201 is, thus, substantially similar to the mounting system 101 described with respect to FIG. 3, but includes a different bearing apparatus 210.

The bearing apparatus 210 shown in FIG. 4 includes a first bearing component 212 which may be formed in, or as a separate component mounted within, the housing 102. The first bearing component 212 includes an arcuate bearing surface 214 which, in one embodiment, may be configured as a substantially spherical surface (i.e., a portion of a sphere). The bearing component 212 may include a substrate 216 and a table 218 formed of a superhard material such as, for example, polycrystalline diamond. In the embodiment shown in FIG. 4, the bearing surface 214 is formed in the table 218.

The bearing apparatus 210 further includes a second bearing component 220 which may be formed directly in, or as a separate component that is coupled with, the back end of cutting element 14. The second bearing component 220 includes an arcuate bearing surface 222. In one embodiment, the arcuate bearing surface 222 may be configured to substantially conform with the shape of the bearing surface 214 of the first bearing component 212. In another embodiment, the arcuate bearing surface 218 of the second bearing component 220 may exhibit a substantially smaller radius (as seen in the cross-sectional view of FIG. 4) than the arcuate bearing surface 214 of the first bearing component 212 such that a limited point or line of contact exists between the two components 212 and 220. As with the first bearing component 212, the second bearing component 220 may include a substrate 224 (e.g., comprising cobalt and tungsten carbide) and a table 226 of a superhard material (e.g., polycrystalline diamond). In the embodiment shown in FIG. 4, the bearing surface 222 is formed in the table 226.

As noted above, the cutting element assembly 200 and mounting system 201 include a number of similarities to the embodiment described in conjunction with FIG. 3. For example, the fastener 106 may be configured with a head 116 having a lower arcuate surface to engage with a mating seat 130. Additionally, a spring retainer 132 may be associated with the spherical seat (either as a separate or integrated component). The seat 130, along with the spring retainer 132, provides another bearing surface which may reduce friction between the cutting element 14 (including the fastener 106) and the housing 102.

Additionally, the mounting system 201 further includes one or more seals 140 and 142 which may be configured as described above. A vibrational member 150 may also be coupled between the bit body 12 and the cutting element 14 to facilitate rotation of the cutting element 14 within the housing 102 when cutting forces are applied to the cutting element 14 during operation of the drill bit 10 as previously discussed. It is also noted that, as with the previously described embodiments, the bearing components 212 and 220 may each include a single component, or a plurality of components cooperatively arranged about the axis of rotation 152 of the cutting element 14.

Figure 5:
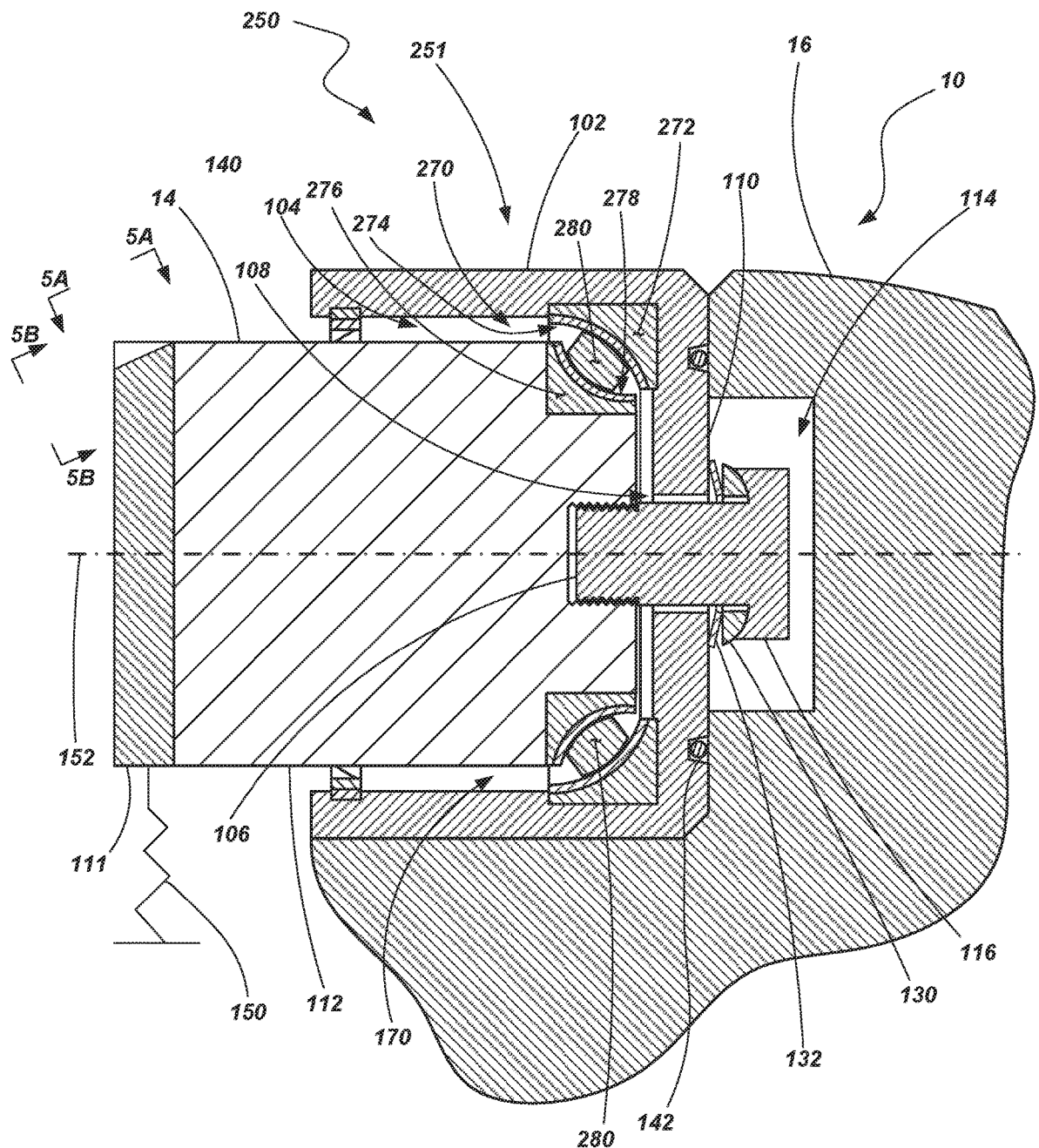
FIG. 5 is a cross-sectional view of a bearing assembly including a mounting system for mounting a cutting element to a drill bit in accordance with another embodiment of the present invention.

Referring to FIG. 5, a cutting element assembly 250, including a mounting system 251, is shown in accordance with another embodiment. The mounting system 251 includes a housing 102 having a cavity 104 formed therein for receipt of a cutting element 14. The housing 102 of the system may be positioned in pocket or recess formed within the bit body 12 and brazed or otherwise fixed to the bit body 12. The cavity 104 and cutter 14 may be configured such that a clearance gap remains between the inner sidewall surface of the housing and the outer side surface of the cutting element as seen in FIG. 4.

A mechanical fastener 106 may be used to retain the cutting element 14 within the cavity 104 of the housing 102. For example, a fastener 106 may extend through an opening 108 formed within a rear wall 110 of the housing and threadably engage a substrate 112 (or other component, such as a base member coupled with the substrate) of the cutting element 14. A cavity or pocket 114 may be formed in the bit body 12 (e.g., within a blade 16) to accommodate the head 116 of the fastener 106. The mounting system 201 is, thus, generally similar to the mounting systems of previously described embodiments but includes a different bearing apparatus 270.

The bearing apparatus 270 shown in FIG. 5 includes a first bearing component 272 formed in, or mounted within, the housing 102. The first bearing component 272 includes an arcuate bearing surface 274 which, in one embodiment, may be configured as a substantially spherical surface (i.e., a portion of a sphere). The bearing surface 274 may be formed, for example, as a polycrystalline diamond surface, although other materials may be employed to provide a low friction and/or wear resistant surface. When formed as a polycrystalline diamond surface, such a structure may be formed using HPHT processes such as described above (e.g., with respect to forming a diamond table 111) or using chemical vapor deposition (CVD) processes. Examples of CVD processes are described in U.S. Pat. Nos. 5,439,492, 4,707,384 and 4,645,977, the disclosures of which are each incorporated by reference herein in their entireties.

The bearing apparatus 270 further includes a second bearing component 276 which may be formed in, or coupled with, the back end of cutting element 14. The second bearing component 276 also includes an arcuate bearing surface 278 which, in one embodiment, may be configured as a substantially spherical surface (i.e., a portion of a sphere). In the embodiment shown in FIG. 5, both arcuate bearing surfaces are formed as concave arcuate surfaces (in contrast to the embodiments described above where one surface was formed as a concave surface and the other as a convex surface). As with the bearing surface 274 of the first component 272, the bearing surface 278 of the second component 276 may comprise a polycrystalline diamond surface or may incorporate other high-strength, wear resistant and/or low friction materials. The bearing apparatus 270 further includes a third component 280 which may be formed as at least one roller element—or rather as a plurality of roller elements. Thus, the bearing apparatus 270 may be configured as a spherical roller bearing apparatus with the first bearing element 272 acting as a first bearing race and the second bearing component 276 acting as a second bearing race, and a plurality of roller elements 280 being positioned between the two races.

As noted above, the cutting element assembly 250 and mounting system 251 include a number of similarities to the embodiment described in conjunction with FIG. 3. For example, the fastener 106 may be configured with a head 116 having a lower arcuate surface to engage with a mating seat 130. Additionally, a spring retainer 132 may be associated with the seat 130 (either as a separate or integrated component). The seat 130, along with the spring retainer 132, provides another bearing surface between the cutting element 14 and the housing 102.

Additionally, the mounting system 251 further includes a first seal 140 and a second seal which may be configured as described above. A vibrational member 150 may also be coupled between the bit body 12 and the cutting element 14 to facilitate rotation of the cutting element 14 within the housing 102 when cutting forces are applied to the cutting element 14 during operation of the drill bit 10 as previously discussed.

Again, the mounting system 251 provides the cutting element 14 with a spherical radial and thrust bearing combination with the housing being mounted to the drill bit 10 rather than the cutting element being mounted directly to the drill bit body. The support structure that is provided to the cutting element 14 relative to the housing enables the movement necessary for the cutting element to vibrate during drilling operations without impeding rotation of the cutting element 14 within the housing and, thus, relative to the bit body 12. The sealed environment enables the cutting element and bearings to be lubricated and, optionally, pressure compensated.

Figure 6A:
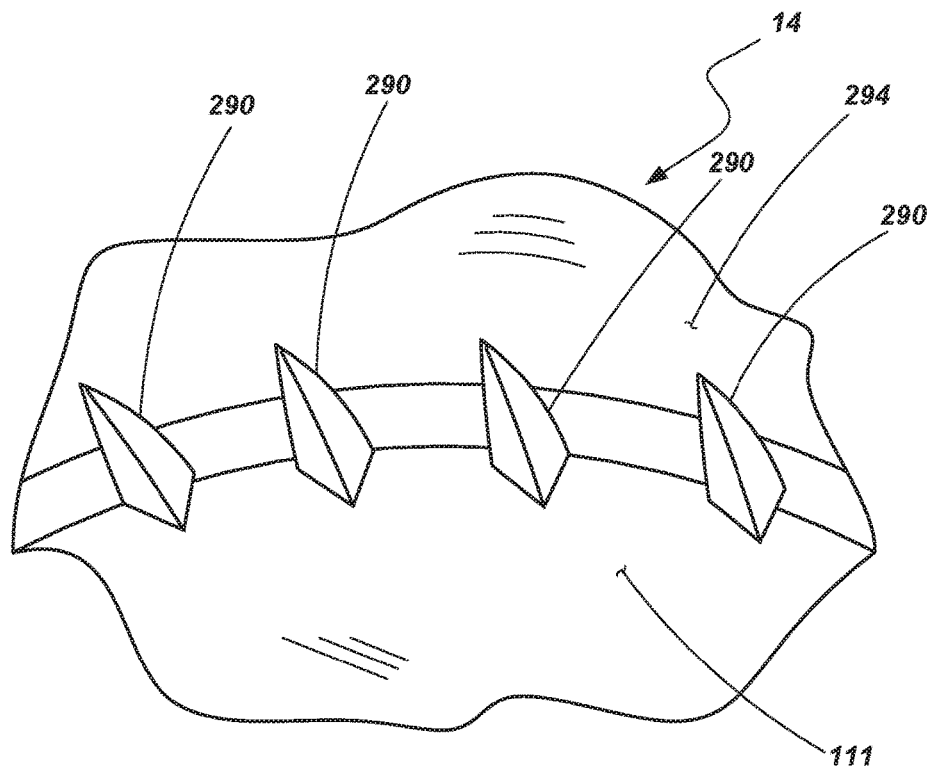
FIGS. 6A and 6B are views of a portion of a cutting element that may be used in conjunction with various mounting systems according to an embodiment of the present invention.
Figure 6B:
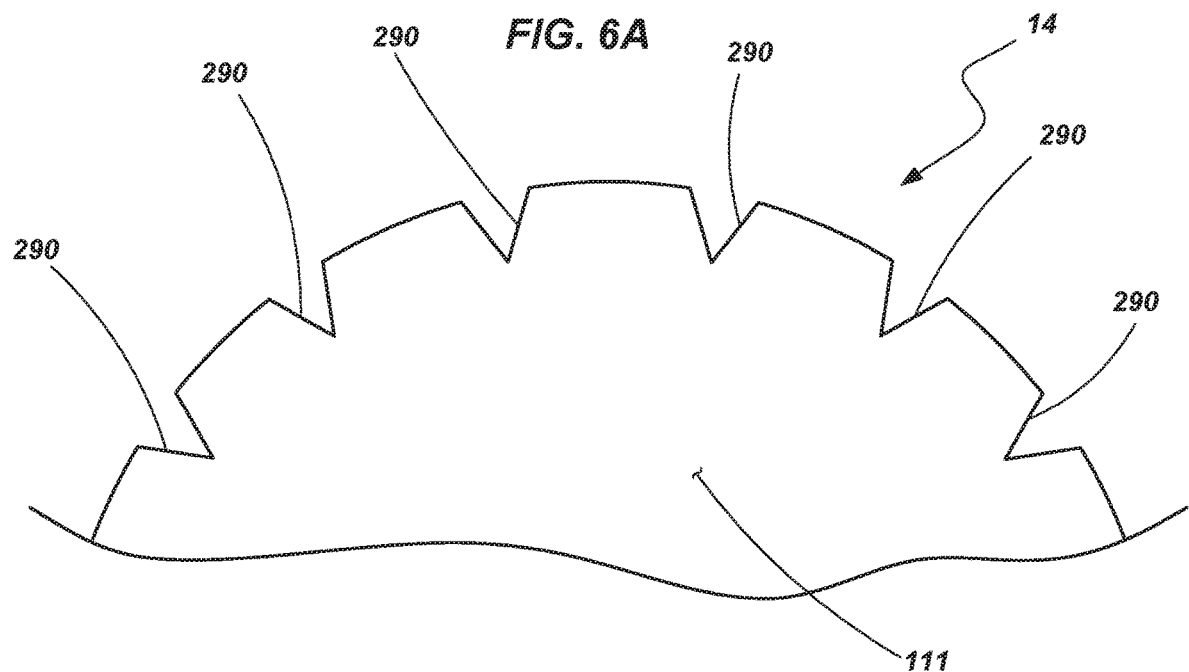

As seen in FIG. 5, and as further detailed in FIGS. 6A and 6B, the cutting element 14 may include a plurality of grooves or flutes 290 formed in a surface of the cutting element 14. For example, multiple flutes 290 may be formed in the superabrasive table 111 along a periphery between an upper surface 292 and a side surface 294 of the cutting element 14. In one embodiment, the flutes 290 may be at least partially formed in a chamfer that is located between the upper surface 292 and the side surface 294. The flutes 290 may be formed at a defined angle relative to a longitudinal axis extending through the cutter 14 (e.g., about axis 152). In certain embodiments, the flutes 210 may be curved or arcuate. During operation of the drill bit 10, as the cutter 14 engages a formation, the formation may interact with the flutes 290 so as to encourage rotation of the cutter 14 in a desired direction relative to the housing 102. Additional examples of cutting elements that may be used are described in U.S. Pat. No. 7,762,359 to Miess, issued Jul. 27, 2010, the disclosure of which is incorporated by reference in its entirety. Any cutter disclosed herein may be used with any described embodiment without limitation.

Figure 7:
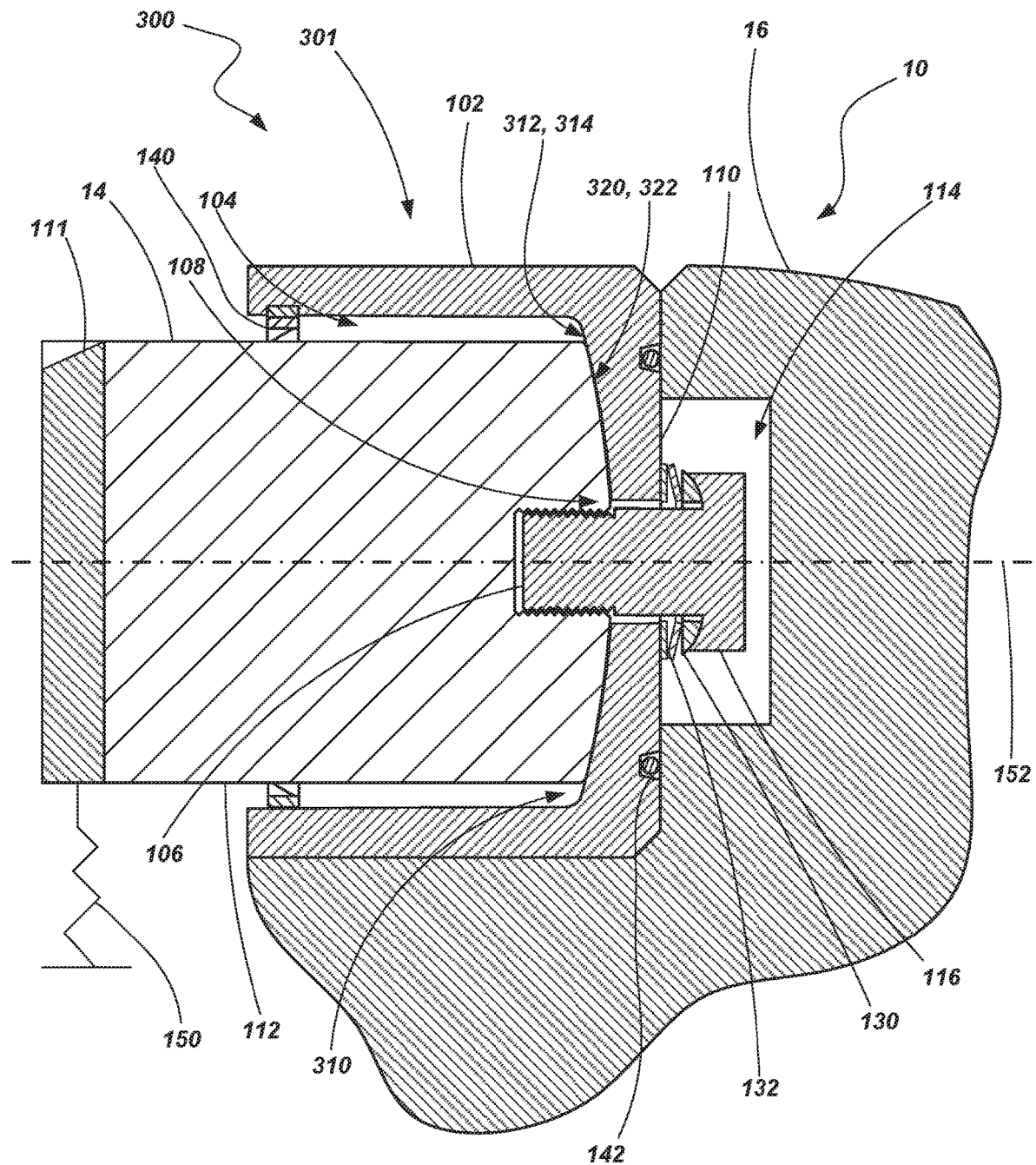
FIG. 7 is a cross-sectional view of a bearing assembly including a mounting system for mounting a cutting element to a drill bit in accordance with yet another embodiment of the present invention.

Referring to FIG. 7, another embodiment of a cutting element assembly 300 and mounting system 301 is shown. The mounting system 301 includes a housing 102 having a cavity 104 formed therein for receipt of a cutting element 14. The housing 102 of the system may be positioned in pocket or recess formed within the bit body 12 and brazed or otherwise fixed to the bit body 12. The cavity 104 and cutter 14 may be configured such that a clearance gap remains between the inner sidewall surface of the housing and the outer side surface of the cutting element. A mechanical fastener 106 may be used to retain the cutting element 14 within the cavity 104 of the housing 102. For example, a fastener 106 may extend through an opening 108 formed within a rear wall 110 of the housing and threadably engage a substrate 112 (or other component, such as a base member coupled with the substrate) of the cutting element 14. A cavity or pocket 114 may be formed in the bit body 12 (e.g., within a blade 16) to accommodate the head 116 of the fastener 106. The mounting system 301 further includes a bearing apparatus 310 to facilitate movement of the cutting element 14 relative to the housing 102.

The bearing apparatus 310 shown in FIG. 7 includes a first bearing component 312 which includes one or more surfaces formed directly in the housing 102. For example, the first bearing component 312 includes a first arcuate bearing surface 314 formed in a wall of the housing 102. In one embodiment, the first bearing surface 314 may be configured as a substantially spherical surface (i.e., a portion of a sphere). The bearing apparatus 310 further includes a second bearing component 320 which includes one more surfaces formed directly on a rear portion of the cutting element 14. For example, the rear portion of the cutting element 14 may include a second arcuate bearing surface 322 configured to engage the first arcuate bearing surface 314. In one embodiment, the second bearing surface 322 may be configured to substantially conform with the shape of the first bearing surface 314. In other embodiments, the second arcuate bearing surface 322 may exhibit a substantially smaller radius than the first arcuate bearing surface 314 such that a limited point or line of contact exists between the two surfaces.

As noted above, the cutting element assembly 300 and mounting assembly 301 include a number of similarities to the embodiments described above. For example, the fastener 106 may be configured with a head 116 having a lower arcuate surface to engage with a mating seat 130. Additionally, a spring retainer 132 may be associated with the seat 130 (either as a separate or integrated component). The seat 130, along with the spring retainer 132, provides another bearing surface to reduce friction between the cutting element 14 (including the fastener 106) and the housing 102.

Additionally, the mounting system 301 further includes one or more seals which may be configured as described above. A vibrational member 150 may also be coupled between the bit body 12 and the cutting element 14 to facilitate rotation of the cutting element 14 within the housing 102 when cutting forces are applied to the cutting element 14 during operation of the drill bit 10 as previously discussed.

Figure 8:
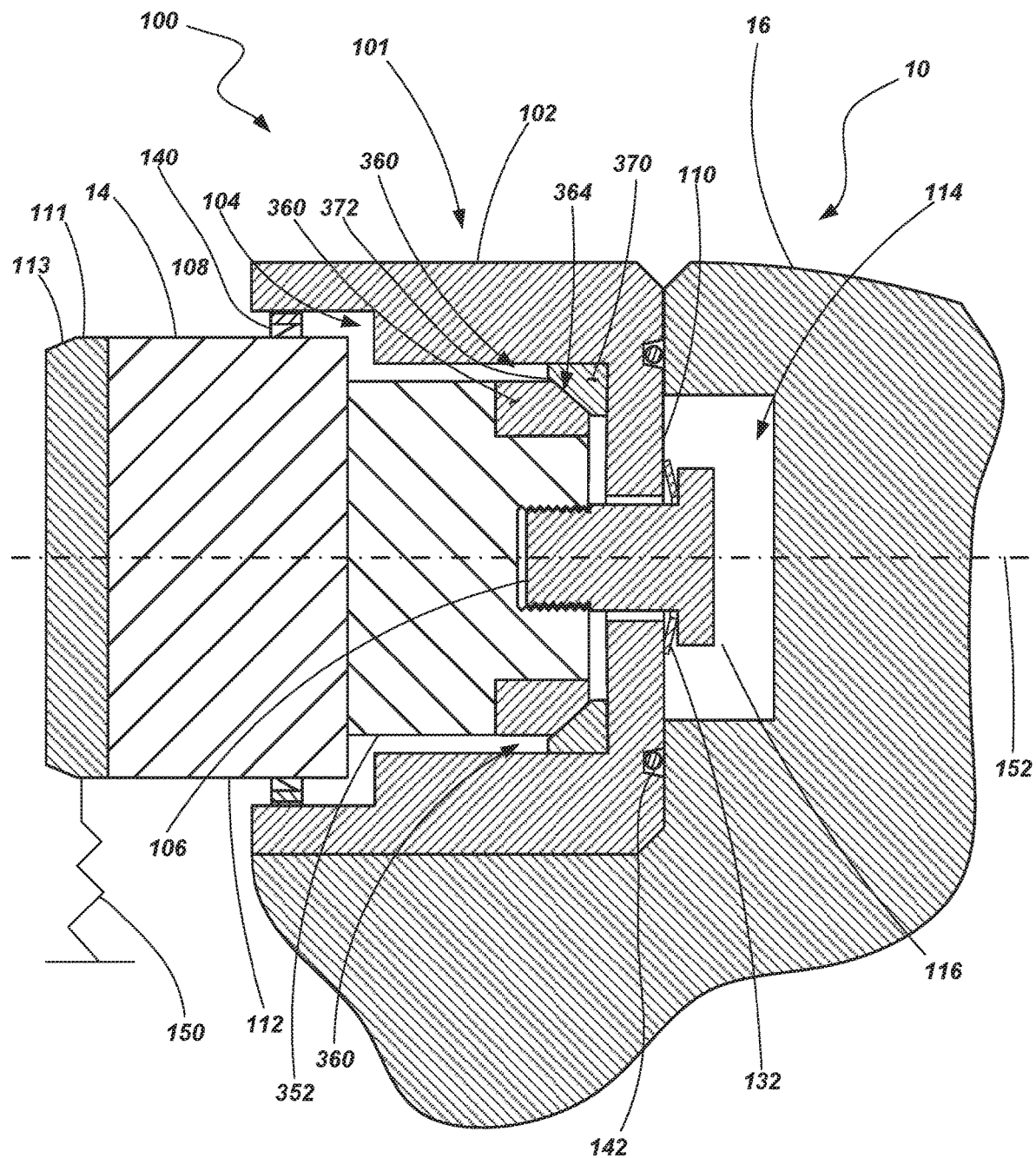
FIG. 8 is a cross-sectional view of a bearing assembly including a mounting system for mounting a cutting element to a drill bit in accordance with a further embodiment of the present invention.

Referring to FIG. 8, another cutting element assembly 350 that includes a mounting system 351 is shown. The mounting system 351 includes a housing 102 having a cavity 104 formed therein for receipt of a cutting element 14. The housing 102 of the system may be positioned in pocket or recess formed within the bit body 12 and brazed or otherwise fixed to the bit body 12. As shown in FIG. 8, the cutting element 14 may include a chamfer 113 located between the upper surface of the table and the side surface of the table 111. Such a feature may also be included in any of the other embodiments disclosed herein.

In the embodiment shown in FIG. 8, the cutting element 14 includes a stepped portion 352. The stepped portion 352 may be a portion of the substrate 112 that is reduced in cross-sectional size (e.g., reduced in diameter) or may include a base member that is bonded to, or otherwise coupled with, the substrate. The cavity 104 and cutter 14 may be configured such that a clearance gap (e.g., a substantially annular gap) remains between the inner sidewall surface of the housing and the outer side surface of the cutting element 14. In the embodiment shown in FIG. 8, the clearance gap is stepped, substantially paralleling the stepped configuration of the cutter 14.

A mechanical fastener 106 may be used to retain the cutting element 14 within the cavity 104 of the housing 102. For example, a fastener 106 may extend through an opening 108 formed within a rear wall 110 of the housing and threadably engage a substrate 112 (or other component, such as a base member coupled with the substrate) of the cutting element 14. A cavity or pocket 114 may be formed in the bit body 12 (e.g., within a blade 16) to accommodate the head 116 of the fastener 106.

The mounting system 351 additionally includes a bearing apparatus 360. The bearing apparatus 360 includes a first bearing component 362 which may be directly formed in, or as a separate component mounted within, the housing 102. The first bearing component 362 includes bearing surface 364 which, in one embodiment, may be configured as a substantially frustoconical surface (i.e., a surface of a truncated cone). This tapered bearing surface 364 may act as a radial bearing surface, a thrust bearing surface, or both. In one embodiment, the bearing component 362 may be formed of a high strength bearing material (e.g., steel, ceramic), while in another embodiment, the bearing component may include a substrate and a table, the table being formed of a superhard material such as, for example, polycrystalline diamond. When formed to include a superhard table, the bearing surface 364 may be formed in the superhard table.

The bearing apparatus 360 further includes a second bearing component 370 which may be formed directly in, or as a separate component that is coupled with (e.g., bonded or brazed to), the back end of cutting element 14. The second bearing component 370 includes a bearing surface 372 for engagement with the bearing surface 362 of the first bearing component 360. In one embodiment, the bearing surface 372 may also be substantially frustoconical and configured to substantially conform with the bearing surface 364 of the first bearing component 362. As with the first bearing component 362, the second bearing component 370 may be formed of a variety of high strength bearing materials or may be configured to include a substrate and a table of a superhard material such as polycrystalline diamond. Also, as with previously described embodiments, the bearing components 362 and 370 may each be formed as a single component, or as a plurality of discrete components cooperatively arranged about the axis of rotation 152 to form a collective bearing surface.

As noted above, the cutting element assembly 350 and mounting assembly 351 include a number of similarities to the embodiments described above. For example, the fastener 106 may be configured with a head 116 that engages a spring retainer 132. Additionally, the mounting system 351 may further include one or more seals 140 and 142 which may be configured as described above. A vibrational member 150 may also be coupled between the bit body 12 and the cutting element 14 to facilitate rotation of the cutting element 14 within the housing 102 when cutting forces are applied to the cutting element 14 during operation of the drill bit 10 as previously discussed.

Figure 9:
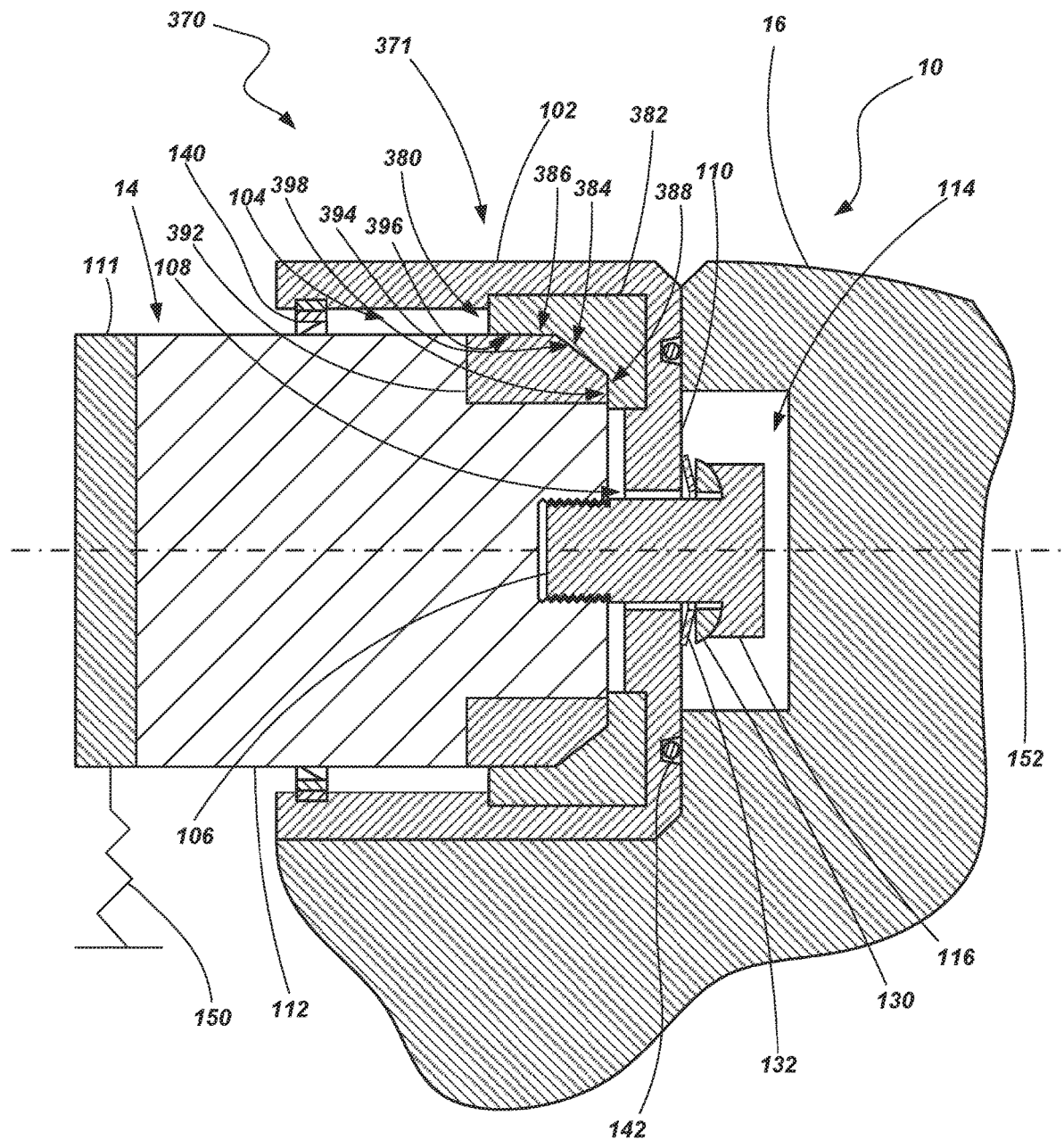
FIG. 9 is a cross-sectional view of a bearing assembly including a mounting system for mounting a cutting element to a drill bit in accordance with another embodiment of the present invention.

Referring to FIG. 9, another cutting element assembly 370 that includes a mounting system 371 is shown. The mounting system 371 includes a housing 102 having a cavity 104 formed therein for receipt of a cutting element 14. The housing 102 of the system may be positioned in pocket or recess formed within the bit body 12 and brazed or otherwise fixed to the bit body 12. The cavity 104 and cutting element 14 may be configured such that a clearance gap (e.g., a substantially annular gap) remains between the inner sidewall surface of the housing and the outer side surface of the cutting element 14.

A mechanical fastener 106 may be used to retain the cutting element 14 within the cavity 104 of the housing 102. For example, a fastener 106 may extend through an opening 108 formed within a rear wall 110 of the housing 102 and threadably engage a substrate 112 (or other component, such as a base member coupled with the substrate) of the cutting element 14. A cavity or pocket 114 may be formed in the bit body 12 (e.g., within a blade 16) to accommodate the head 116 of the fastener 106.

The mounting system 371 additionally includes a bearing apparatus 380. The bearing apparatus 380 includes a first bearing component 382 which may be directly formed in, or as a separate component mounted within, the housing 102. The first bearing component 382 includes a first bearing surface 384 which, in one embodiment, may be configured as a substantially frustoconical surface (i.e., a surface of a truncated cone), a second surface 386 which is primarily configured as a radial bearing surface, and a third surface 388 which is primarily configured as a thrust bearing surface. In one embodiment, the bearing component 382 may be formed of a high strength bearing material (e.g., steel, ceramic), while in another embodiment, the bearing component 382 may include a substrate and a table, the table being formed of a superhard material such as, for example, polycrystalline diamond. When formed to include a superhard table, the bearing surface 364 may be formed in the superhard table.

The bearing apparatus 380 further includes a second bearing component 392 which may be formed directly in, or as a separate component that is coupled with (e.g., bonded or brazed to), the back end of cutting element 14 (e.g., the substrate of the cutting element 14). The second bearing component 392 includes a first bearing surface 394 for engagement with the first bearing surface 384 of the first bearing component 382. The second bearing component 392 may also include a second surface 396 for engagement with the second surface 386 of the first bearing component 382, and a third surface 398 for engagement with the third surface 388 of the first bearing component 382. The various surfaces (394, 396 and 398) of the second component 392, or portions thereof, may be configured to be substantially complimentary in geometry with associated surfaces (384, 386, and 388) of the first bearing component 382. For example, the first surface 394 of the second bearing component 392 may be configured as a substantially frustoconical surface (i.e., a surfaces of a truncated cone) to mate with the first surface 384 (or a portion) of the first bearing component 382.

As with the first bearing component 382, the second bearing component 392 may be formed of a variety of high strength bearing materials or may be configured to include a substrate and a table of a superhard material such as polycrystalline diamond. Also, as with previously described embodiments, the bearing components 382 and 392 may each be formed as a single component, or as a plurality of discrete components cooperatively arranged about the axis of rotation 152 to form a collective bearing surface.

As noted above, the cutting element assembly 370 and mounting assembly 371 include a number of similarities to the embodiments described above. For example, the fastener 106 may be configured with a head 116 that engages a mating seat 130 and spring retainer 132. Additionally, the mounting system 371 may further include one or more seals 140 and 142 which may be configured as described above. A vibrational member 150 may also be coupled between the bit body 12 and the cutting element 14 to facilitate rotation of the cutting element 14 within the housing 102 when cutting forces are applied to the cutting element 14 during operation of the drill bit 10 as previously discussed.

As noted above, the cutting element assembly 350 and mounting assembly 351 include a number of similarities to the embodiments described above. For example, the fastener 106 may be configured with a head 116 that engages a spring retainer 132. Additionally, the mounting system 351 may further include one or more seals 140 and 142 which may be configured as described above. A vibrational member 150 may also be coupled between the bit body 12 and the cutting element 14 to facilitate rotation of the cutting element 14 within the housing 102 when cutting forces are applied to the cutting element 14 during operation of the drill bit 10 as previously discussed.

Figure 10:
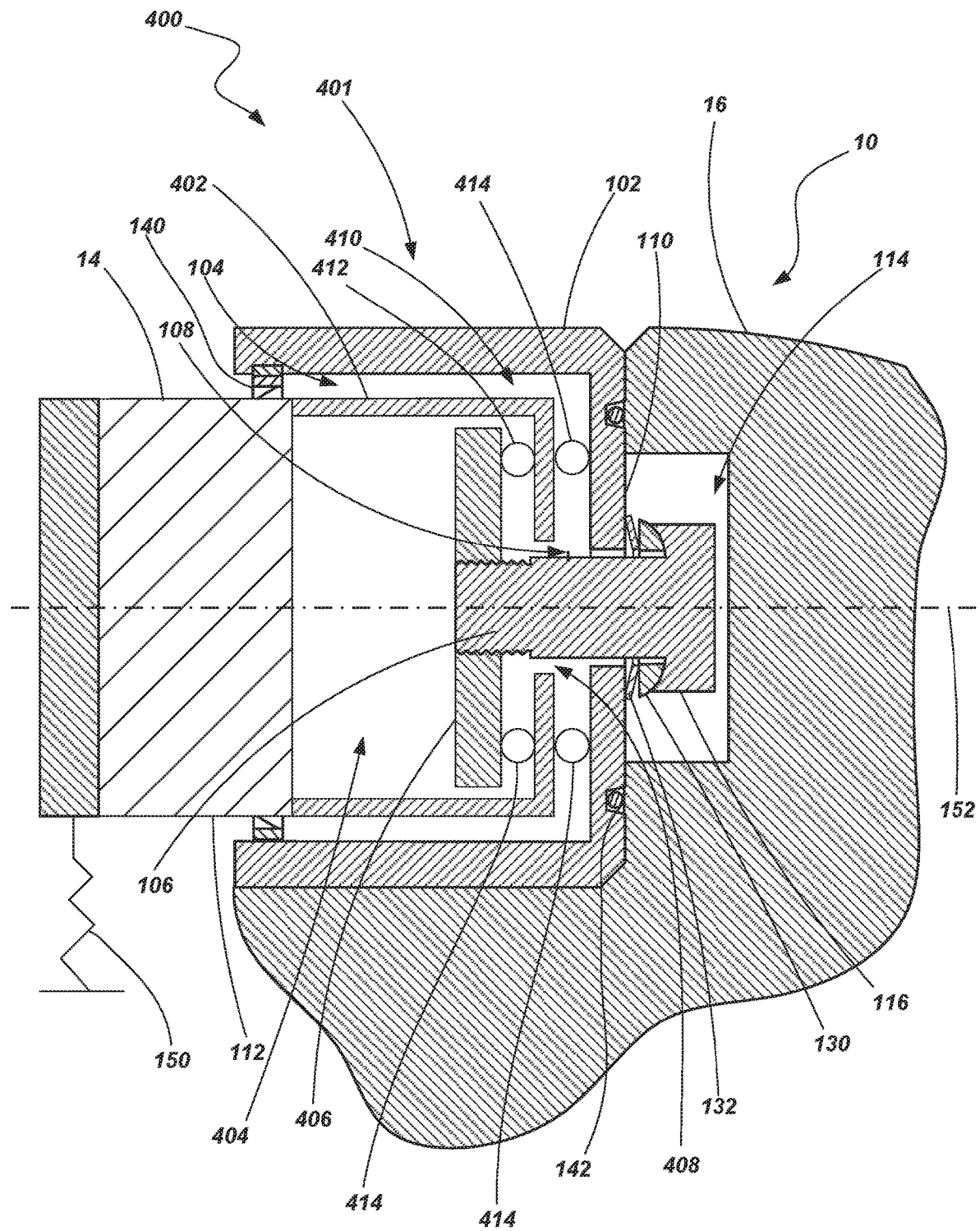
FIG. 10 is a cross-sectional view of a bearing assembly including a mounting system for mounting a cutting element to a drill bit in accordance with another embodiment of the present invention.

Referring to FIG. 10, a cutting element assembly 400 including a mounting system 401 is shown in accordance with another embodiment. The mounting system 401 includes a housing 102 having a cavity 104 formed therein for receipt of a cutting element 14. The housing 102 of the system may be positioned in a pocket or recess formed within the bit body 12 and brazed or otherwise fixed to the bit body 12. The cavity 104 and cutter 14 may be configured such that a clearance gap remains between the inner sidewall surface of the housing and the outer side surface of the cutting element 14. The cutting element 14 includes a base member 402 coupled with the substrate. The base member 402 defines an internal pocket or cavity 404 in which a first structural component, referred to herein as an anchor member 406, is disposed. Another structural element, such as a mechanical fastener 106 extends through a through-hole 408 formed in the base member 402 and is coupled with the anchor member 406. The anchor member 404 is sized and configured such that it is retained within the cavity 404 and does not pass through the through hole 408 of the base member 402. As with previously described embodiments, a cavity or pocket 114 may be formed in the bit body 12 to accommodate the head 116 of the fastener 106.

The mounting system 401 additionally includes a bearing apparatus 410. The bearing apparatus 410 includes a first plurality of bearing elements 412, disposed between the anchor member 406 and an internal surface of the base member 402. The first bearing elements 412 may be configured, for example, as a plurality of ball bearings or roller bearings with the anchor member 406 and the base member 402 servings as bearing components, specifically, acting as bearing races. The bearing apparatus 410 further includes a second plurality of bearing elements 414 disposed between an outer surface of the base member 402 and an internal surface of the housing 102. The second set of bearing elements 414 may likewise be formed as ball bearings or roller bearings with the base member 402 and the housing serving as bearing components, specifically acting as bearing races in the illustrated embodiment.

As noted above, the cutting element assembly 400 and mounting system 401 include a number of similarities to the embodiments described above. For example, the fastener 106 may be configured with a head 116 having a lower arcuate surface to engage with a mating seat 130. Additionally, a spring retainer 132 may be associated with the seat 130 (either as a separate or integrated component). The seat 130, along with the spring retainer 132, provides another bearing surface between the cutting element 14 (including the fastener 106) and the housing 102.

Additionally, the mounting system 401 includes one or more seals 140 and 142 which may be configured as described above. A vibrational member 150 may also be coupled between the bit body 12 and the cutting element 14 to facilitate rotation of the cutting element 14 within the housing 102 when cutting forces are applied to the cutting element 14 during operation of the drill bit 10 as previously discussed.

Again, the mounting system 401 provides a housing that is mounted to the drill bit 10 with the cutting element 14 mounted to the housing by way of a bearing assembly. The support structure that is provided to the cutting element 14 relative to the housing enables the movement necessary for the cutting element to vibrate during drilling operations without impeding rotation of the cutting element 14 within the housing and, thus, relative to the bit body 12. The sealed environment enables the cutting element and bearings to be lubricated and, optionally, pressure compensated.

Figure 11:
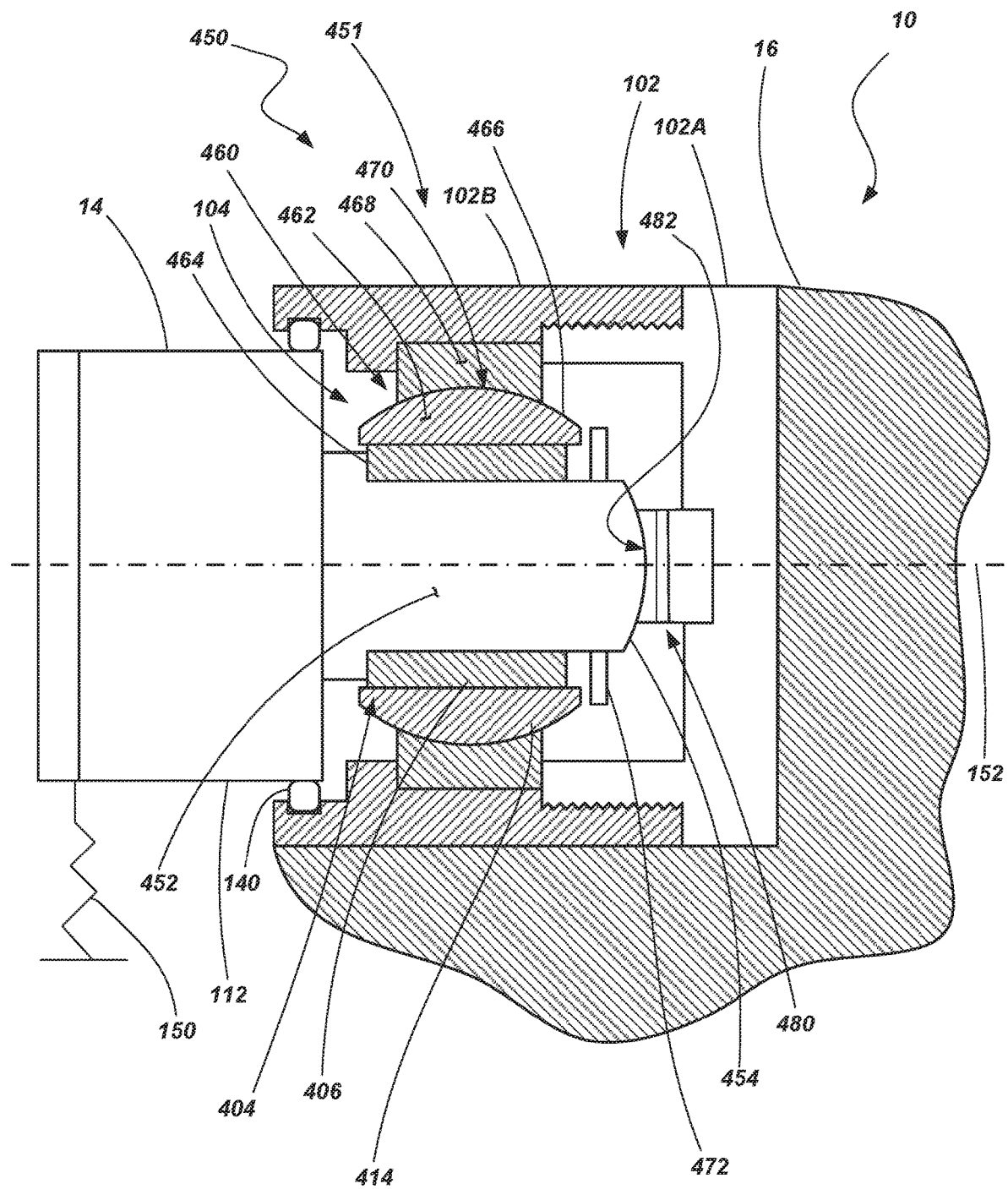
FIG. 11 is a cross-sectional view of a bearing assembly including a mounting system for mounting a cutting element to a drill bit in accordance with yet another embodiment of the present invention.

Referring to FIG. 11, a cutting element assembly 450 including a mounting system 451 is shown in accordance with another embodiment. The mounting system 451 includes a housing 102 having a cavity 104 formed therein for receipt of a cutting element 14. The housing 102 of the system may be positioned in pocket or recess formed within the bit body 12 and brazed or otherwise fixed to the bit body 12. The cavity 104 defined by the housing 102 and the cutter 14 may be configured such that a clearance gap remains between the inner sidewall surface of the housing and the outer side surface of the cutting element.

In one embodiment, the housing may be formed of multiple components. For example, the housing 102 may include a first component 102A and a second component 102B that are threadably coupled with one another. In such a case, one component (e.g., the first component 102A) may be brazed or otherwise fixed to the bit body while the other component (e.g., the second component 102B) may be removably coupled with the first component enabling a user to perform maintenance on, replace, or repair various components of the cutting element assembly 450.

The cutting element 14 may include a stepped portion 452. In one embodiment the stepped portion 452 is configured as a base member that is bonded, adhered or otherwise coupled with the substrate 112. In another embodiment, the stepped portion 452 may be an integral component of the substrate that is shaped and sized to a desired geometric configuration for engagement with other components of the mounting assembly 451 (e.g., bearing apparatus 460). The rear surface 454 of the stepped portion may include an arcuate surface as shown in FIG. 10. For example, in one embodiment, the rear surface 454 may be substantially spherical.

The mounting system 451 additionally includes a bearing apparatus 460. The bearing apparatus 460 includes a first bearing component 462 that encircles a portion of the stepped portion 452. One or more bearing elements 464, such as, for example, a sleeve bearing or a plurality of roller bearing elements, such as needle bearings, may be disposed between the stepped portion 452 and the first bearing element 462 in an arrangement encircling the stepped portion 452 so as to enable low friction rotation of the cutting element 14 about a rotational axis 152. The first bearing component 462 includes an arcuate outer surface 466 which, in one embodiment, may be generally convex and substantially spherical. A second bearing component 468 is mounted within the housing 102 (e.g., mounted between a shoulder of the first housing component 102A and a shoulder of the second housing component 102B) and includes an internal arcuate bearing surface 470. The internal arcuate bearing surface 470 is configured to engage the arcuate outer surface 466 of the first bearing component 462. Thus, in one embodiment, the internal arcuate bearing surface 470 may also be configured as a substantially spherical surface. The arcuate surface 466 of the first bearing component 462 and the arcuate surface 470 of the second component 468 enable the cutting element 14 to pivot or move relative to the housing 102. In other words, the bearing apparatus 460 enables the cutting element to rotate about the defined axis 152, while also allowing the axis 152 to be displaced (or change angles) relative to the housing 102 and the drill bit body 12.

An anchor member 472 may be coupled with the stepped portion 452 and be sized and configured to retain the cutting element 14 in its position relative to the bearing apparatus 460. Thus, if the cutting element 14 is displaced in a direction toward the opening of the cavity (away from the first housing component 102A), the anchor member 472 will abut a portion of the bearing apparatus (e.g., the first bearing component 462) and prevent the cutting element 14 from becoming dislocated from the housing 102.

As with other embodiments, the bearing components may be formed of a variety of materials. In one example, at least one of the bearing components (e.g., 462, 464 and 468) may be formed of steel while at least one of the other bearing components may be formed of a copper alloy (e.g., a copper-tin-nickel alloy such as Toughmet®). In one embodiment, the copper alloy material may be further coated with another material such as, for example, silver.

The mounting system 451 may additionally include a third bearing component 480 that engages the rear surface 454 of the stepped portion 452. The third bearing component 480 may include an arcuate surface 482 (e.g., a substantially spherical surface) that engages a complimentary shaped rear surface 454 of the stepped portion 452. The third bearing component 480 may be a discrete component mounted within the housing 102, or it may be integrally formed within the housing 102. In one embodiment, a biasing mechanism (e.g., a spring or an elastomer material) may be associated with the third bearing component 480 to maintain a biasing force against the cutting element 14.

The mounting system 451 may further include various features such as described with other embodiments such one or more seals. Additionally, a vibrational member 150 may be coupled between the bit body 12 and the cutting element 14 to facilitate rotation of the cutting element 14 within the housing 102 when cutting forces are applied to the cutting element 14 during operation of the drill bit 10 as previously discussed.

Again, the mounting system 451 provides a housing that is mounted to the drill bit 10 with the cutting element 14 mounted to the housing by way of a bearing assembly. The support structure that is provided to the cutting element 14 relative to the housing enables the movement necessary for the cutting element to vibrate during drilling operations without impeding rotation of the cutting element 14 within the housing and, thus, relative to the bit body 12. The sealed environment enables the cutting element and bearings to be lubricated and, optionally, pressure compensated.

Enabling the cutting element 14 to rotate relate to its housing 102 (and, thus, relative to the drill bit body 12) may significantly decrease wear on cutting element 14, thereby significantly increasing the usable life of cutting element 14 in comparison with conventional cutting elements. As cutting element 14 rotates relative to cutting pocket 27, a surface portion of cutting element 14 exposed to a formation during drilling may be periodically changed, or substantially continuously changed, in contrast to a conventional cutting element, where the surface portion of a conventional cutting element exposed to a formation remains constant. Rotation of cutting element 14 during a drilling operation may expose a greater portion of cutting element 14 to the formation being drilled, which may reduce wear of the cutting element 14. For example, the volume of diamond worn away from cutting element 14 for a given volume of rock cut may be reduced in comparison with a conventional non-rotatable cutting element.

In various embodiments, the cutting element 14 may be substantially cylindrical and, as noted above, configured to rotated about its central axis 152. The cutting element 14 be rotated about axis 152 in a clockwise direction, in a counter-clockwise direction, or both (i.e., serially). The cutting element 14 may be rotated in at least one or more directions, intermittently or substantially continuously, so that various portions of the cutting element interact with a material being cut during drilling or other cutting operation.

Figure 12:
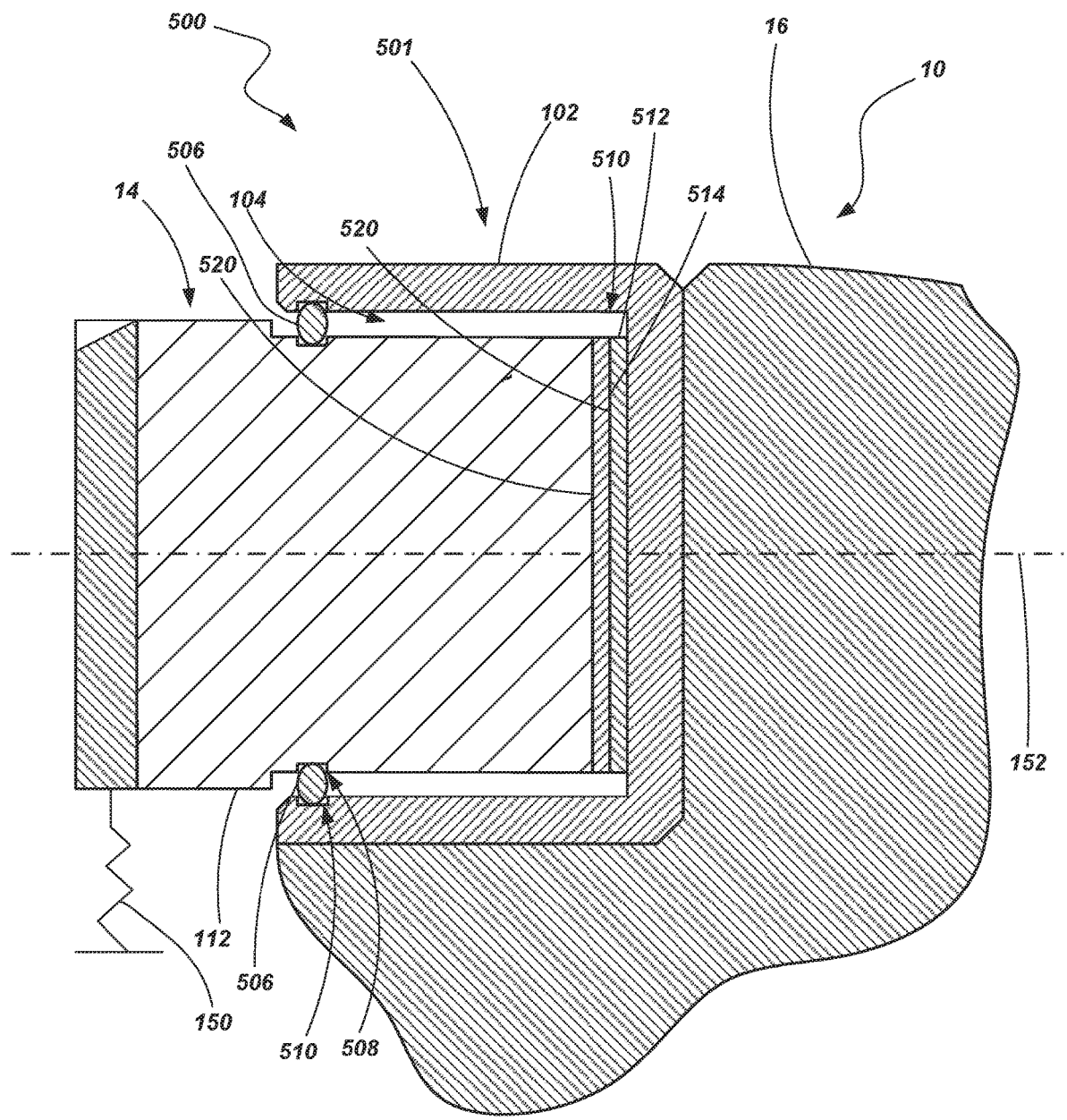
FIG. 12 is a cross-sectional view of a bearing assembly including a mounting system for mounting a cutting element to a drill bit in accordance with another embodiment of the present invention.

Referring to FIG. 12, another embodiment of a cutting element assembly 500 and mounting system 501 is shown. The mounting system 501 includes a housing 102 having a cavity 104 formed therein for receipt of a cutting element 14. The housing 102 of the system may be positioned in pocket or recess formed within the bit body 12 and brazed or otherwise fixed to the bit body 12. The cavity 104 and cutter 14 may be configured such that a clearance gap remains between the inner sidewall surface of the housing 102 and the outer side surface of the cutting element 14. A mechanical fastener may be used to retain the cutting element 14 within the cavity 104 of the housing 102. For example, a circlip 506 or other retaining member may be used to retain the cutting element 14 in a desired position relative to the housing 102. The circlip 506 may be partially disposed within a substantially annular groove 508 formed in the housing 102 and partially disposed within a substantially annular groove 510 formed in a portion of the cutting element 14 (e.g., within the substrate 112). The mounting system 501 further includes a bearing apparatus 510 to facilitate movement of the cutting element 14 relative to the housing 102.

The bearing apparatus 510 shown in FIG. 12 includes a first bearing component 512 which includes one or more surfaces formed directly in the housing 102. For example, the first bearing component 512 includes a first substantially planar bearing surface 514 formed in a wall of the housing 102. The bearing apparatus 510 further includes a second bearing component 520 which includes one more surfaces formed directly on a rear portion of the cutting element 14. For example, the rear portion of the cutting element 14 may include a second substantially planar bearing surface 522 configured to engage the first substantially planar bearing surface 514. In other embodiments, the bearing surfaces of the two bearing components 512 and 520 may be configured to exhibit non-planar bearing surfaces including, for example, portions of a surface of a sphere.

A vibrational member 150 may also be coupled between the bit body 12 and the cutting element 14 to facilitate rotation of the cutting element 14 within the housing 102 about a rotational axis 152 when cutting forces are applied to the cutting element 14 during operation of the drill bit 10 as previously discussed. While not specifically shown, the mounting system 501 may include one or more additional features or components (such as described with other embodiments set forth herein) including any combination of one or more seals, a lubrication system, and/or a pressure compensation system.

Various factors may affect the rotation of cutting element 14 in the housing 102, including the extent and/or speed of rotation of the cutting element 14 relative to housing 102. These factors may include, without limitation, the size of cutting element 14, the size of housing 102, the size of the clearance gap between the cutting element 14 and the housing 102, and/or vibrational frequencies and magnitudes resulting from cutting forces acting on rotary drill bit 10. Accordingly, the rotation of the cutting element 14 may be configured to suit various drilling situations and to maximize the usable life of the cutting element 14.

One of ordinary skill in the art will appreciate that the discussed methods and structures could be used for varied applications as known in the art, without limitation. In addition, while certain embodiments and details have been included herein for purposes of illustrating aspects of the instant disclosure, it will be apparent to those skilled in the art that various changes in the systems, apparatuses, and methods disclosed herein may be made without departing from the scope of the instant disclosure, which is defined, at least in part, in the appended claims. Features and components described with regard to one embodiment may be combined with other embodiments, or with features and components of other embodiments, without limitation. The words "including" and "having," as used herein, including the claims, shall have the same meaning as the word "comprising."

What is claimed is:

1. A method of drilling a subterranean formation, the method comprising:
   providing a drill bit having a body, a first cutting insert coupled with the body via a first mounting system wherein the first mounting system to includes a housing having a pocket formed therein and housing at least a portion of the first cutting insert;
   providing at least one radial bearing component between the first cutting insert and the housing;
   providing at least one thrust bearing component between the first cutting insert and the housing;
   providing a seal between the housing and the first cutting insert;
   engaging a subterranean formation with the drill bit while rotating the drill bit about a first rotational axis;
   rotating the first cutting insert about a second rotational axis relative to the housing while rotating the drill bit about the first rotational axis;
   maintaining a substantially annular clearance gap located between the housing and the first cutting insert and extending from the seal towards the at least one thrust bearing component while rotating the first cutting insert about the second rotational axis.

2. The method according to claim 1, further comprising enabling the second rotational axis to vary angularly relative to the housing.

3. The method according to claim 2, further comprising coupling at least a second cutting insert with the body via a second mounting system.

4. The method according to claim 3, further comprising configuring the second mounting system to include at least one radial bearing component between the at least a second cutting insert and the housing of the at least one mounting system and at least one thrust bearing component between the at least a second cutting insert and the housing of the at least a second mounting system.

5. The method according to claim 2, further comprising retaining the first cutting insert within the pocket with a retaining member.

6. The method according to claim 1, further comprising pressurizing the pocket.

7. The method according to claim 1, further comprising providing a plurality of grooves formed in a peripheral region of the cutting insert.

8. The method according to claim 7, wherein the plurality of grooves are each at least partially formed in a side surface of the cutting insert.

9. The method according to claim 1, further comprising providing the housing with a first housing component and a second housing component, and threadably coupling the first housing component with the second housing component.

10. The method according to claim 9, further comprising brazing the first housing component to the bit body.

11. The method according to claim 1, further comprising brazing the housing to the bit body.

12. The method according to claim 1, further comprising lubricating the at least one radial bearing component.

13. The method according to claim 1, further comprising configuring the at least one radial bearing component to exhibit a substantially spherical bearing surface.

14. The method according to claim 1, further comprising that at least one of the radial bearing component and the thrust bearing component is configured as a tapered bearing component.

15. The method according to claim 1, further comprising retaining the first cutting insert within the cavity by threadably coupling a retaining member with first cutting insert and positioning a spherical seat member between the retaining member and a portion of the housing.

16. The method according to claim 1, wherein at least one of the at least one radial bearing component and the at least one thrust bearing component includes a rolling element.

17. The method according to claim 1, further comprising providing the first cutting insert to include a table of superhard material bonded to a substrate, wherein a bearing surface is formed in the table of superhard material.

18. A method of drilling a subterranean formation, the method comprising:
   providing a drill bit having a body, a first cutting insert coupled with the body via a first mounting system wherein the first mounting system to includes a housing having a pocket formed therein and housing at least a portion of the first cutting insert;
   providing at least one bearing component between the first cutting insert and the housing; engaging a subterranean formation with the drill bit while rotating the drill bit about a first rotational axis;
   rotating the first cutting insert about a second rotational axis relative to the housing while rotating the drill bit about the first rotational axis;
providing pressure compensation within the pocket in response to a change in external pressure experienced by the drill bit while the drill bit is engaging the subterranean formation.

* * * * *